(12) United States Patent
Kim et al.

(10) Patent No.: US 12,428,543 B2
(45) Date of Patent: Sep. 30, 2025

(54) CONNECTED MEDICAL DEVICE CONTAINING A LIQUID CRYSTALLINE POLYMER COMPOSITION HAVING A LOW DIELECTRIC CONSTANT

(71) Applicant: Ticona LLC, Florence, KY (US)

(72) Inventors: Young Shin Kim, Cincinnati, OH (US); Philip T. Wilson, Cincinnati, OH (US); Don DeMello, Salado, TX (US)

(73) Assignee: Ticona LLC, Florence, KY (US)

( * ) Notice: Subject to any disclaimer, the term of this patent is extended or adjusted under 35 U.S.C. 154(b) by 362 days.

(21) Appl. No.: 17/732,592

(22) Filed: Apr. 29, 2022

(65) Prior Publication Data

US 2022/0389195 A1 Dec. 8, 2022

Related U.S. Application Data

(60) Provisional application No. 63/189,971, filed on May 18, 2021.

(51) Int. Cl.
*C08K 13/04* (2006.01)
*A61B 5/00* (2006.01)
*A61B 5/0205* (2006.01)
*A61B 5/024* (2006.01)
(Continued)

(52) U.S. Cl.
CPC ............ *C08K 13/04* (2013.01); *A61B 5/0015* (2013.01); *A61B 5/02055* (2013.01); *A61B 5/024* (2013.01); *A61B 5/1451* (2013.01); *A61B 5/14542* (2013.01); *A61B 5/14546* (2013.01); *A61B 5/4875* (2013.01); *A61B 5/6801* (2013.01); *A61B 5/6898* (2013.01); *C08G 63/19* (2013.01)

(58) Field of Classification Search
CPC ... A61B 5/0015; A61B 5/02055; A61B 5/024; A61B 5/1451; A61B 5/14542; A61B 5/14546; A61B 5/6801; A61B 5/4875; A61B 5/6898
See application file for complete search history.

(56) References Cited

U.S. PATENT DOCUMENTS

| 4,161,470 A | 7/1979 | Calundann |
| 4,693,253 A | 9/1987 | Adams |
| 5,616,680 A | 4/1997 | Linstid, III |
| (Continued) | | |

FOREIGN PATENT DOCUMENTS

| CN | 110383578 A | 10/2019 |
| CN | 209679245 U | 11/2019 |
| (Continued) | | |

OTHER PUBLICATIONS

Youhao Yang, U.S. Appl. No. 17/867,777, filed Jul. 19, 2022, Drug Delivery Pump.

(Continued)

*Primary Examiner* — Brian T Gedeon
(74) *Attorney, Agent, or Firm* — Dority & Manning, P.A.

(57) ABSTRACT

A medical device capable of transmitting a radiofrequency signal to and/or receiving a radiofrequency signal from an external device is provided. The medical device comprises at least one component that contains a polymer composition that exhibits a dielectric constant of about 6 or less at a frequency of 2 GHz, wherein the polymer composition includes a liquid crystalline polymer.

42 Claims, 2 Drawing Sheets

(51) Int. Cl.
  *A61B 5/145* (2006.01)
  *C08G 63/19* (2006.01)

(56) References Cited

U.S. PATENT DOCUMENTS

| | | | |
|---|---|---|---|
| 5,739,193 A | 4/1998 | Walpita et al. |
| 5,987,352 A | 11/1999 | Klein et al. |
| 6,114,492 A | 9/2000 | Linstid, III |
| 6,230,059 B1 | 5/2001 | Duffin |
| 6,412,490 B1 | 7/2002 | Lee |
| 6,514,611 B1 | 2/2003 | Shepherd et al. |
| 6,522,525 B1 | 2/2003 | O'Phelan et al. |
| 6,643,552 B2 | 11/2003 | Edell et al. |
| 6,684,102 B1 | 1/2004 | O'Phelan et al. |
| 6,723,052 B2 | 4/2004 | Mills |
| 6,730,377 B2 | 5/2004 | Wang |
| 6,855,115 B2 | 2/2005 | Fonseca et al. |
| 7,044,972 B2 | 5/2006 | Mathys, Jr. et al. |
| 7,101,597 B2 | 9/2006 | Wang |
| 7,147,604 B1 | 12/2006 | Allen et al. |
| 7,190,569 B2 | 3/2007 | O'Phelan et al. |
| 7,277,755 B1 | 10/2007 | Falkenberg et al. |
| 7,387,826 B2 | 6/2008 | Burgmeier et al. |
| 7,403,823 B1 | 7/2008 | Kroll et al. |
| 7,491,188 B2 | 2/2009 | Holman et al. |
| 7,496,408 B2 | 2/2009 | Ghanem et al. |
| 7,548,784 B2 | 6/2009 | Chinchoy |
| 7,582,078 B2 | 9/2009 | Chen et al. |
| 7,620,453 B1 | 11/2009 | Propato et al. |
| 7,640,058 B2 | 12/2009 | Lang |
| 7,662,129 B2 | 2/2010 | Chen |
| 7,672,723 B2 | 3/2010 | Veillette et al. |
| 7,766,394 B2 | 8/2010 | Sage et al. |
| 7,842,024 B2 | 11/2010 | Burgmeier et al. |
| 7,857,785 B2 | 12/2010 | Chen |
| 7,899,520 B2 | 3/2011 | Lian et al. |
| 7,914,485 B2 | 3/2011 | Chen et al. |
| 7,937,161 B2 | 5/2011 | Hastings et al. |
| 7,959,900 B2 | 6/2011 | Peng et al. |
| 7,976,557 B2 | 7/2011 | Kunis |
| 7,985,234 B2 | 7/2011 | Wang et al. |
| 8,012,208 B2 | 9/2011 | Lechmann et al. |
| 8,043,673 B2 | 10/2011 | Lee et al. |
| 8,050,774 B2 | 11/2011 | Kveen et al. |
| 8,052,996 B2 | 11/2011 | Lautenbach et al. |
| 8,060,198 B2 | 11/2011 | Lian et al. |
| 8,126,545 B2 | 2/2012 | Flach et al. |
| 8,150,502 B2 | 4/2012 | Kumar et al. |
| 8,160,682 B2 | 4/2012 | Kumar et al. |
| 8,180,460 B2 | 5/2012 | Nevsmith et al. |
| 8,187,492 B2 | 5/2012 | Chen |
| 8,200,330 B2 | 6/2012 | Kroll et al. |
| 8,209,023 B2 | 6/2012 | Zhou et al. |
| 8,244,335 B2 | 8/2012 | Kumar et al. |
| 8,265,741 B2 | 9/2012 | Whittington et al. |
| 8,352,025 B2 | 1/2013 | Jacobson |
| 8,463,393 B2 | 6/2013 | Strother et al. |
| 8,496,616 B2 | 7/2013 | Chen |
| 8,497,342 B2 | 7/2013 | Chen et al. |
| 8,509,896 B2 | 8/2013 | Doerr et al. |
| 8,509,898 B2 | 8/2013 | Hauer et al. |
| 8,538,503 B2 | 9/2013 | Kumar et al. |
| 8,577,466 B2 | 11/2013 | Mashiach |
| 8,612,021 B2 | 12/2013 | Seifert et al. |
| 8,655,425 B2 | 2/2014 | Kim et al. |
| 8,798,745 B2 | 8/2014 | Jacobson |
| 8,886,277 B2 | 11/2014 | Kim et al. |
| 8,886,305 B2 | 11/2014 | Doerr et al. |
| 8,923,963 B2 | 12/2014 | Bonner et al. |
| 8,945,017 B2 | 2/2015 | Venkatraman et al. |
| 8,951,426 B2 | 2/2015 | Brindley et al. |
| 8,954,140 B2 | 2/2015 | Mottaiyan et al. |
| D725,276 S | 3/2015 | Fitzsimons et al. |
| 9,020,608 B2 | 4/2015 | Swanson |
| 9,022,962 B2 | 5/2015 | Brown |
| 9,168,384 B2 | 10/2015 | Askarinya et al. |
| 9,173,670 B2 | 11/2015 | Sepulveda et al. |
| D744,659 S | 12/2015 | Bishay et al. |
| 9,199,086 B2 | 12/2015 | Zielinski et al. |
| 9,241,649 B2 | 1/2016 | Kumar et al. |
| 9,241,829 B2 | 1/2016 | Basinger et al. |
| 9,345,414 B1 | 5/2016 | Bardy et al. |
| D759,725 S | 6/2016 | Akana et al. |
| 9,364,155 B2 | 6/2016 | Bardy et al. |
| 9,375,580 B2 | 6/2016 | Bonner et al. |
| 9,380,956 B2 | 7/2016 | Bera et al. |
| 9,468,739 B2 | 10/2016 | Sutherland et al. |
| 9,526,433 B2 | 12/2016 | Lapetina et al. |
| 9,536,122 B2 | 1/2017 | Potyrailo |
| 9,545,228 B2 | 1/2017 | Bardy et al. |
| 9,554,715 B2 | 1/2017 | Bardy et al. |
| 9,687,666 B2 | 6/2017 | Jacobson |
| D800,596 S | 10/2017 | Ling et al. |
| 9,808,633 B2 | 11/2017 | Bonner et al. |
| 9,861,809 B2 | 1/2018 | Greenberg et al. |
| 9,872,999 B2 | 1/2018 | Jacobson |
| D809,510 S | 2/2018 | Rochat et al. |
| 9,996,678 B2 | 6/2018 | Johnson |
| 10,106,682 B2 | 10/2018 | Kim |
| 10,178,973 B2 | 1/2019 | Venkatraman et al. |
| 10,238,883 B2 | 3/2019 | Jacobson |
| 10,409,226 B2 | 9/2019 | Balti et al. |
| 10,426,952 B2 | 10/2019 | Kveen et al. |
| 10,433,852 B2 | 10/2019 | H'Doubler |
| 10,478,617 B2 | 11/2019 | Pepin et al. |
| 10,500,393 B2 | 12/2019 | Kim et al. |
| 10,603,486 B2 | 3/2020 | Walker et al. |
| 10,709,889 B2 | 7/2020 | Thyagarajan |
| 10,780,222 B2 | 9/2020 | Ward et al. |
| 10,788,753 B2 | 9/2020 | Cole |
| 10,852,855 B2 | 12/2020 | Niu et al. |
| 10,894,165 B2 | 1/2021 | Min |
| 10,942,491 B2 | 3/2021 | Rothkopf et al. |
| 10,967,122 B2 | 4/2021 | Cima |
| 11,026,628 B1 | 6/2021 | Bruinsma et al. |
| 11,052,260 B2 | 7/2021 | Doguet et al. |
| 11,081,045 B2 | 8/2021 | Park et al. |
| 11,096,601 B2 | 8/2021 | Hong et al. |
| 11,110,271 B1 | 9/2021 | Schobben et al. |
| 11,129,986 B2 | 9/2021 | Schobben et al. |
| 11,134,851 B2 | 10/2021 | Houck et al. |
| 11,154,247 B2 | 10/2021 | Drasler et al. |
| 11,179,102 B2 | 11/2021 | Shimuta |
| D940,881 S | 1/2022 | Hadley et al. |
| 11,229,383 B2 | 1/2022 | Pikov et al. |
| 11,399,726 B2 | 8/2022 | Campo et al. |
| 11,705,641 B2* | 7/2023 | Kim ............... H01Q 21/0087 |
| | | 343/702 |
| 2004/0135118 A1 | 7/2004 | Waggoner |
| 2006/0241759 A1 | 10/2006 | Trieu |
| 2007/0103311 A1 | 5/2007 | Kippelen et al. |
| 2007/0231681 A1 | 10/2007 | Casby et al. |
| 2008/0015494 A1 | 1/2008 | Santini et al. |
| 2008/0033500 A1 | 2/2008 | Strother et al. |
| 2008/0183133 A1 | 7/2008 | Kiersh |
| 2008/0203358 A1 | 8/2008 | Mizumoto et al. |
| 2008/0293999 A1 | 11/2008 | Halahmi |
| 2012/0172818 A1 | 7/2012 | Harms et al. |
| 2012/0190813 A1 | 7/2012 | Taguchi |
| 2012/0209365 A1 | 8/2012 | Seifert et al. |
| 2013/0106659 A1* | 5/2013 | Yung ............... H05K 1/0373 |
| | | 524/424 |
| 2013/0237906 A1 | 9/2013 | Park et al. |
| 2014/0100426 A1 | 4/2014 | Barbour |
| 2014/0135469 A1 | 5/2014 | Kim et al. |
| 2014/0139385 A1* | 5/2014 | Yoon ............... H01Q 9/0414 |
| | | 343/904 |
| 2014/0249612 A1 | 9/2014 | Bonmassar et al. |
| 2014/0378781 A1 | 12/2014 | Peluso et al. |
| 2015/0148356 A1 | 5/2015 | Marat et al. |
| 2015/0148757 A1 | 5/2015 | Aeschlimann |
| 2015/0175805 A1 | 6/2015 | Schaefer |
| 2015/0257663 A1 | 9/2015 | Deliwala |
| 2015/0267315 A1 | 9/2015 | Schiller et al. |

(56) References Cited

U.S. PATENT DOCUMENTS

| | | |
|---|---|---|
| 2015/0291796 A1 | 10/2015 | Kim |
| 2016/0114145 A1 | 4/2016 | Cook et al. |
| 2016/0206881 A1* | 7/2016 | Libbus ............... A61N 1/36139 |
| 2016/0237311 A1 | 8/2016 | Mizori |
| 2017/0002137 A1 | 1/2017 | Nair |
| 2017/0029682 A1* | 2/2017 | Kim ........................ C08K 3/38 |
| 2018/0179345 A1 | 6/2018 | Al-Harthi et al. |
| 2018/0187077 A1 | 7/2018 | Lee |
| 2019/0018087 A1 | 1/2019 | Hahn et al. |
| 2019/0076097 A1 | 3/2019 | Edouard |
| 2019/0159371 A1* | 5/2019 | Grinsteinner ......... G01S 7/4813 |
| 2019/0166733 A1 | 5/2019 | Gogotsi et al. |
| 2019/0169247 A1 | 6/2019 | Kim |
| 2019/0169427 A1 | 6/2019 | Kim |
| 2020/0247970 A1* | 8/2020 | Chen ........................ C08J 5/244 |
| 2020/0268271 A1 | 8/2020 | Hadley |
| 2020/0283683 A1 | 9/2020 | Yakacki |
| 2020/0301255 A1 | 9/2020 | Kim |
| 2021/0057811 A1 | 2/2021 | Kim |
| 2021/0070983 A1 | 3/2021 | Kim et al. |
| 2021/0093209 A1 | 4/2021 | Chang et al. |
| 2021/0093861 A1 | 4/2021 | Raje et al. |
| 2021/0153791 A1 | 5/2021 | Liu et al. |
| 2021/0186422 A1 | 6/2021 | Nielsen et al. |
| 2021/0251488 A1 | 8/2021 | English et al. |
| 2021/0386353 A1 | 12/2021 | Hadley et al. |
| 2022/0035900 A1 | 2/2022 | Flakne et al. |
| 2022/0062649 A1 | 3/2022 | Schobben et al. |
| 2022/0212016 A1 | 7/2022 | Yaffe |
| 2022/0380674 A1 | 12/2022 | Kim et al. |
| 2022/0386870 A1 | 12/2022 | Kim et al. |

FOREIGN PATENT DOCUMENTS

| | | |
|---|---|---|
| CN | 110755730 A | 2/2020 |
| CN | 214873129 U | 11/2021 |
| JP | 2019134053 A | 8/2019 |
| JP | 2019147913 A | 9/2019 |
| KR | 1144532 | 5/2012 |
| KR | 1956849 | 3/2019 |
| WO | WO 2004/014456 A2 | 2/2004 |
| WO | WO 2008/041619 A1 | 4/2008 |
| WO | WO 2010/017238 A1 | 2/2010 |
| WO | WO 2020/092469 A2 | 5/2020 |
| WO | WO 2020/190569 A1 | 9/2020 |
| WO | WO 2021034882 A1 | 2/2021 |
| WO | WO 2021/097383 A1 | 5/2021 |
| WO | WO 2023/014942 | 2/2023 |

OTHER PUBLICATIONS

International Search Report and Written Opinion for PCT/US2022/29417, dated Jul. 27, 2022, 9 pages.
Related Application Form.
Toray Plastics, Impact Properties, 6 pages.
Supplementary European Search Report for EP 22 80 5251 dated Mar. 13, 2025, 8 pages.

* cited by examiner

CONNECTED MEDICAL DEVICE CONTAINING A LIQUID CRYSTALLINE POLYMER COMPOSITION HAVING A LOW DIELECTRIC CONSTANT

RELATED APPLICATION

The present application is based upon and claims priority to U.S. Provisional Patent Application Ser. No. 63/189,971, having a filing date of May 18, 2021, which is incorporated herein by reference.

BACKGROUND OF THE INVENTION

Connected medical devices are devices that can transmit data to and/or from an external device (e.g., heartrate monitor that transmits a patient's heartrate data to a physician's tablet via Bluetooth®). The data is generally transmitted using an antenna system that is configured to transmit radiofrequency ("RF") signals at a variety of frequencies, including Wireless Medical Telemetry Service (WMTS), Bluetooth, LTE, and 5G frequencies. The ability to quickly and accurately transmit and receive data via an RF signal, however, may be affected by a variety of factors, including signal artifacts and other electrical noise. The manner in which the medical device is employed may also reduce the quality of the transmitted RF signal. For example, when the medical device is employed in a wearable device, the user's motion and movement can also reduce the quality of the RF signal. Of course, various steps can be taken to try and reduce signal noise, but ultimately it would be desirable if the medical device itself could be configured in such a way that the signal noise had a minimal impact on the detection of the RF signal. As such, a need currently exists for connected medical devices having a lower degree of signal loss.

SUMMARY OF THE INVENTION

In accordance with one embodiment of the present invention, a medical device is disclosed that is capable of transmitting a radiofrequency signal to and/or receiving a radiofrequency signal from an external device. The medical device comprises at least one component that contains a polymer composition that exhibits a dielectric constant of about 6 or less at a frequency of 2 GHz, wherein the polymer composition includes a liquid crystalline polymer.

Other features and aspects of the present invention are set forth in greater detail below.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which.

DETAILED DESCRIPTION

Figure 1:
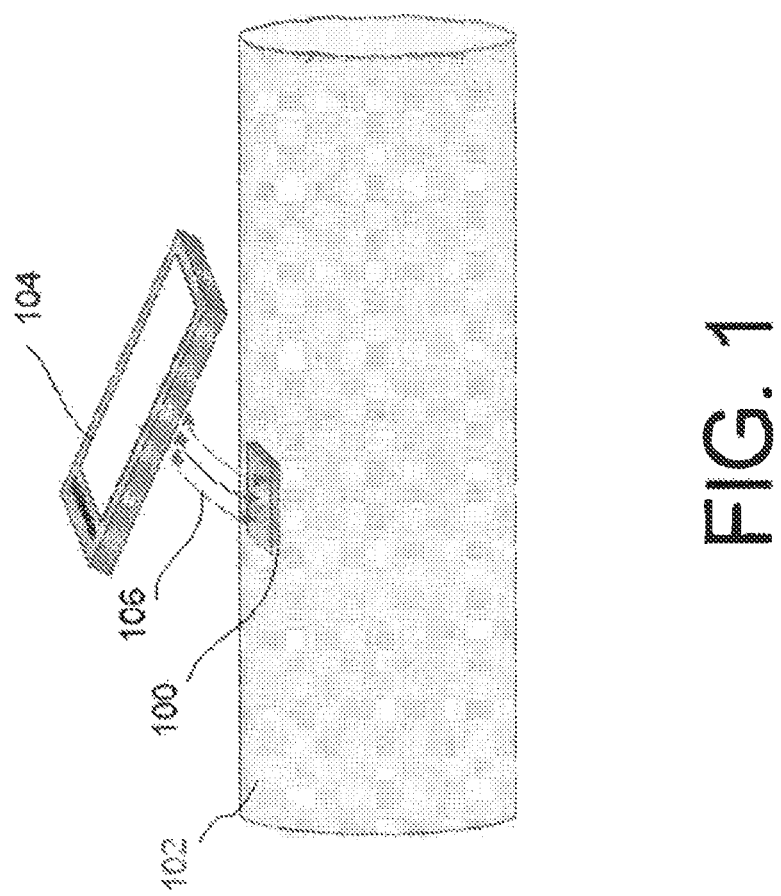
FIG. 1 is a perspective view of one embodiment of the medical device (e.g., glucose monitor) of the present invention.

It is to be understood by one of ordinary skill in the art that the present discussion is a description of exemplary embodiments only, and is not intended as limiting the broader aspects of the present invention.

Generally speaking, the present invention is directed to a medical device that is capable of transmitting data to and/or receiving data from an external device, such as a desktop computer, portable electronic device (e.g., laptop, tablet, phone, etc.), wearable device (e.g., smartwatch), and so forth. Examples of such medical devices may include, for instance, sensors that are configured to obtain physiological information (e.g., heart rate, oxygen saturation, chemicals in blood or subcutaneous interstitial fluid (e.g., glucose), body temperature, tissue hydration, etc. Such sensors may be wearable and/or implantable. When employed, the wearable device (e.g., glucose monitor, watch, phone, headband, etc.) may be any electronic device suitable for contact with a body region of an individual, such as a user's skin, wrist, arm, leg, finger, etc. The medical device may also include a drug delivery device, such as an injection pen, autoinjector, infusion pump, subcutaneous injection pump, meter dose inhaler, dry powder inhaler, nasal inhaler, iontophoresis patch, etc. Other suitable medical devices may likewise include telemetric devices, such as those employed for home health or hospital monitoring, CPAP machines, oxygen concentrators, medicine distribution containers, blood pressure cuffs, etc. Regardless of the type, the medical device is generally configured to transmit and/or receive radiofrequency signals at a variety of frequencies, including Wireless Medical Telemetry Service (WMTS), Bluetooth, LTE, and 5G frequencies.

To help reduce the amount of electrical noise encountered by the medical device, at least one component of the medical device contains a polymer composition that contains a liquid crystalline polymer. Examples of components that may employ the polymer composition include, for instance, housings for the entire device and/or or a component thereof, one or more portions of any antenna system (e.g., substrate, window, repeater, etc.), radiofrequency filters, electrical connectors, and so forth. The polymer composition may form only a portion of the component, or alternatively the entire component. Regardless, the polymer composition generally exhibits a low dielectric constant. For example, the polymer composition may exhibit a low dielectric constant, such as about 6 or less, in some embodiments about 5 or less, in some embodiments from about 0.1 to about 4 and in some embodiments, from about 0.5 to about 3.5, and in some embodiments, from about 1 to about 3 at high frequencies (e.g., 2 or 10 GHz). The polymer composition may also exhibit a low dissipation factor (measure of the loss rate of energy), such as about 0.01 or less, in some embodiments about 0.009 or less, in some embodiments about 0.008 or less, in some embodiments, about 0.007 or less, in some embodiments about 0.006 or less, and in some embodiments, from about 0.001 to about 0.005 at high frequencies (e.g., 2 or 10 GHz). Notably, the present inventors have also discovered that the dielectric constant and dissipation factor can be maintained within the ranges noted above even when exposed to various temperatures, such as a temperature of from about −30° C. to about 100° C. For example, when subjected to a heat cycle test as described herein, the ratio of the dielectric constant after heat cycling to the initial dielectric constant may be about 0.8 or more, in some embodiments about 0.9 or more, and in some embodiments, from about 0.91 to about 0.99. Likewise, the ratio of the dissipation factor after being exposed to the high temperature to the initial dissipation factor may be about 1 or less, in some embodiments about 0.95 or less, in some embodiments from about 0.1 to about 0.9, and in some embodiments, from about 0.2 to about 0.8. The change in dissipation factor (i.e., the initial dissipation factor–the dissipation factor after heat cycling) may also range from about −0.1 to about 0.1, in some embodiments from about −0.05 to about 0.01, and in some embodiments, from about −0.001 to 0.

The polymer composition may also provide a high degree of shielding effectiveness to electromagnetic interference ("EMI"). More particularly, the EMI shielding effectiveness may be about 20 decibels (dB) or more, in some embodiments about 25 dB or more, and in some embodiments, from about 30 dB to about 100 dB, as determined in accordance with ASTM D4935-18 at high frequencies (e.g., 2 or 10 GHz).

In addition to exhibiting good electrical properties, the polymer composition may also be formed to have a melt viscosity that is sufficiently low to enable it to be readily molded into the small dimensions required for a medical device. For example, the polymer composition may have a melt viscosity of about 200 Pa-s or less, in some embodiments about 150 Pa-s or less, in some embodiments about 100 Pa-s or less, in some embodiments from about 5 Pa-s to about 90 Pa-s, and in some embodiments, from about 10 to about 70 Pa-s, as determined in accordance with ISO Test No. 11443:2014 at a shear rate of 400 seconds$^{-1}$ at a temperature of about 30° C. above the melting temperature (e.g., about 380° C.). Conventionally, it was believed that polymer compositions exhibiting such a low melt viscosity would not also possess sufficiently good thermal and mechanical properties to enable good physical integrity for use in forming a medical device. Contrary to conventional thought, however, the present inventors have discovered through careful control of the particular liquid crystalline polymer(s) and/or other optional materials, the resulting polymer composition can also possess both excellent thermal and mechanical properties. More particularly, the polymer composition typically has a melting temperature of about 280° C. or more, in some embodiments about 300° C. or more, in some embodiments about 320° C. or more, and in some embodiments, from about 330° C. to about 450° C., such as determined in accordance with ISO 11357-2:2013. Even at such melting temperatures, the ratio of the deflection temperature under load ("DTUL"), a measure of short-term heat resistance, to the melting temperature may still remain relatively high, which can, among other things, allow the use of high-speed processes for forming the medical device. For example, the ratio may range from about 0.5 to about 1.00, in some embodiments from about 0.65 to about 0.95, and in some embodiments from about 0.75 to about 0.85. The specific DTUL values may, for instance, be about 160° C. or more, in some embodiments from about 200° C. to about 350° C., in some embodiments from about 220° C. to about 320° C., and in some embodiments from about 250° C. to about 300° C., such as determined in accordance with ISO Test No. 75-2:2013 (technically equivalent to ASTM D648-07) at a load of 1.8 Megapascals.

The polymer composition may be generally stiff in nature so that it is capable of maintaining the desired degree of physical integrity during formation of the medical device. Such stiffness may be generally characterized by a high tensile modulus. For example, the tensile modulus may be about 8,000 MPa or more, in some embodiments about 10,000 MPa or more, in some embodiments about 11,000 MPa or more, in some embodiments from about 12,000 MPa to about 30,000 MPa, in some embodiments from about 13,000 MPa to about 25,000 MPa, and in some embodiments, from about 14,000 MPa to about 22,000 MPa, such as determined in accordance with ISO Test No. 527:2019 at 23° C. The composition may also exhibit a tensile strength of from about 150 MPa or more, in some embodiments from about 160 to about 400 MPa, and in some embodiments, from about 170 to about 350 MPa and/or a tensile break strain of about 1% or more, in some embodiments about 2% or more, in some embodiments about 3% or more, in some embodiments from about 4% to about 20%, and in some embodiments, from about 5% to about 15%, such as determined in accordance with ISO Test No. 527:2019 at 23° C. The polymer composition may also exhibit a flexural modulus of about 10,000 MPa or more, in some embodiments about 11,000 MPa or more, in some embodiments from about 12,000 MPa to about 30,000 MPa, and in some embodiments, from about 13,000 MPa to about 25,000 MPa; a flexural strength of from about 40 to about 500 MPa, in some embodiments from about 100 to about 400 MPa, and in some embodiments, from about 150 to about 350 MPa; and/or a flexural break strain of about 0.5% or more, in some embodiments from about 1% to about 15%, and in some embodiments, from about 2% to about 10%, such as determined in accordance with ISO Test No. 178:2019 at 23° C. The composition may also exhibit a Charpy unnotched impact strength of about 45 kJ/m$^2$ or more, in some embodiments from about 45 to about 100 kJ/m$^2$, and in some embodiments, from about 50 to about 80 kJ/m$^2$, measured at 23° C. according to ISO Test No. 179-1:2010. The polymer composition may also exhibit excellent surface properties. The polymer composition may, for instance, exhibit a Rockwell surface hardness of about 65 or less, in some embodiments about 60 or less, and in some embodiments, from about 40 to about 55, as determined in accordance with ASTM D785-08 (2015) (Scale M).

Various embodiments of the present invention will now be described in more detail.

I. Polymer Composition

A. Liquid Crystalline Polymer

Liquid crystalline polymers are generally classified as "thermotropic" to the extent that they can possess a rod-like structure and exhibit a crystalline behavior in their molten state (e.g., thermotropic nematic state). Such polymers typically have a melting temperature of about 280° C. or more, in some embodiments about 300° C. or more, in some embodiments about 320° C. or more, and in some embodiments, from about 330° C. to about 450° C. The polymers may be formed from one or more types of repeating units as is known in the art. The liquid crystalline polymer may, for example, contain one or more aromatic ester repeating units generally represented by the following Formula (I):

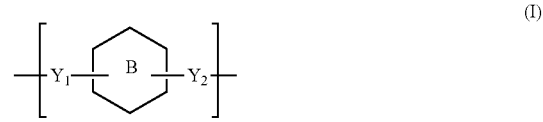

wherein, ring B is a substituted or unsubstituted 6-membered aryl group (e.g., 1,4-phenylene or 1,3-phenylene), a substituted or unsubstituted 6-membered aryl group fused to a substituted or unsubstituted 5- or 6-membered aryl group (e.g., 2,6-naphthalene), or a substituted or unsubstituted 6-membered aryl group linked to a substituted or unsubstituted 5- or 6-membered aryl group (e.g., 4,4-biphenylene); and $Y_1$ and $Y_2$ are independently O, C(O), NH, C(O)HN, or NHC(O).

Typically, at least one of $Y_1$ and $Y_2$ are C(O). Examples of such aromatic ester repeating units may include, for instance, aromatic dicarboxylic repeating units ($Y_1$ and $Y_2$ in Formula I are C(O)), aromatic hydroxycarboxylic repeating units ($Y_1$ is O and $Y_2$ is C(O) in Formula I), as well as various combinations thereof.

Aromatic hydroxycarboxylic repeating units, for instance, may be employed that are derived from aromatic hydroxycarboxylic acids, such as, 4-hydroxybenzoic acid; 4-hydroxy-4'-biphenylcarboxylic acid; 2-hydroxy-6-naphthoic acid; 2-hydroxy-5-naphthoic acid; 3-hydroxy-2-naphthoic acid; 2-hydroxy-3-naphthoic acid; 4'-hydroxyphenyl-4-benzoic acid; 3'-hydroxyphenyl-4-benzoic acid; 4'-hydroxyphenyl-3-benzoic acid, etc., as well as alkyl, alkoxy, aryl and halogen substituents thereof, and combination thereof. Particularly suitable aromatic hydroxycarboxylic acids are 4-hydroxybenzoic acid ("HBA") and 6-hydroxy-2-naphthoic acid ("HNA"). When employed, repeating units derived from hydroxycarboxylic acids (e.g., HBA and/or HNA) typically constitute about 20 mol. % or more, in some embodiments about 25 mol. % or more, in some embodiments about 30 mol. % or more, in some embodiments about 40 mol. % or more, in some embodiments about 50 mol. % or more, in some embodiments from about 55 mol. % to 100 mol. %, and in some embodiments, from about 60 mol. % to about 95 mol. % of the polymer.

Aromatic dicarboxylic repeating units may also be employed that are derived from aromatic dicarboxylic acids, such as terephthalic acid, isophthalic acid, 2,6-naphthalenedicarboxylic acid, diphenyl ether-4,4'-dicarboxylic acid, 1,6-naphthalenedicarboxylic acid, 2,7-naphthalenedicarboxylic acid, 4,4'-dicarboxybiphenyl, bis(4-carboxyphenyl) ether, bis(4-carboxyphenyl)butane, bis(4-carboxyphenyl) ethane, bis(3-carboxyphenyl)ether, bis(3-carboxyphenyl) ethane, etc., as well as alkyl, alkoxy, aryl and halogen substituents thereof, and combinations thereof. Particularly suitable aromatic dicarboxylic acids may include, for instance, terephthalic acid ("TA"), isophthalic acid ("IA"), and 2,6-naphthalenedicarboxylic acid ("NDA"). When employed, repeating units derived from aromatic dicarboxylic acids (e.g., IA, TA, and/or NDA) each typically constitute from about 1 mol. % to about 40 mol. %, in some embodiments from 2 mol. % to about 30 mol. %, and in some embodiments, from about 5 mol. % to about 25 mol. % of the polymer.

Other repeating units may also be employed in the polymer. In certain embodiments, for instance, repeating units may be employed that are derived from aromatic diols, such as hydroquinone, resorcinol, 2,6-dihydroxynaphthalene, 2,7-dihydroxynaphthalene, 1,6-dihydroxynaphthalene, 4,4'-dihydroxybiphenyl (or 4,4'-biphenol), 3,3'-dihydroxybiphenyl, 3,4'-dihydroxybiphenyl, 4,4'-dihydroxybiphenyl ether, bis(4-hydroxyphenyl)ethane, etc., as well as alkyl, alkoxy, aryl and halogen substituents thereof, and combinations thereof. Particularly suitable aromatic diols may include, for instance, hydroquinone ("HQ") and 4,4'-biphenol ("BP"). When employed, repeating units derived from aromatic diols (e.g., HQ and/or BP) typically constitute from about 1 mol. % to about 50 mol. %, in some embodiments from about 1 mol. % to about 40 mol. %, in some embodiments from about 2 mol. % to about 40 mol. %, in some embodiments from about 5 mol. % to about 35 mol. %, and in some embodiments from about 5 mol. % to about 25 mol. % of the polymer.

Repeating units may also be employed, such as those derived from aromatic amides (e.g., acetaminophen ("APAP")) and/or aromatic amines (e.g., 4-aminophenol ("AP"), 3-aminophenol, 1,4-phenylenediamine, 1,3-phenylenediamine, etc.). When employed, repeating units derived from aromatic amides (e.g., APAP) and/or aromatic amines (e.g., AP) typically constitute from about 0.1 mol. % to about 20 mol. %, in some embodiments from about 0.5 mol. % to about 15 mol. %, and in some embodiments, from about 1 mol. % to about 10 mol. % of the polymer. It should also be understood that various other monomeric repeating units may be incorporated into the polymer. For instance, in certain embodiments, the polymer may contain one or more repeating units derived from non-aromatic monomers, such as aliphatic or cycloaliphatic hydroxycarboxylic acids, dicarboxylic acids, diols, amides, amines, etc. Of course, in other embodiments, the polymer may be "wholly aromatic" in that it lacks repeating units derived from non-aromatic (e.g., aliphatic or cycloaliphatic) monomers.

In certain embodiments, the liquid crystalline polymer may be a "high naphthenic" polymer to the extent that it contains a relatively high content of repeating units derived from naphthenic hydroxycarboxylic acids and naphthenic dicarboxylic acids, such as NDA, HNA, or combinations thereof. That is, the total amount of repeating units derived from naphthenic hydroxycarboxylic and/or dicarboxylic acids (e.g., NDA, HNA, or a combination of HNA and NDA) is typically about 10 mol. % or more, in some embodiments about 12 mol. % or more, in some embodiments about 15 mol. % or more, in some embodiments about 18 mol. % or more, in some embodiments about 30 mol. % or more, in some embodiments about 40 mol. % or more, in some embodiments about 45 mol. % or more, in some embodiments 50 mol. % or more, in some embodiments about 55 mol. % or more, and in some embodiments, from about 55 mol. % to about 95 mol. % of the polymer. Without intending to be limited by theory, it is believed that such "high naphthenic" polymers are capable of reducing the tendency of the polymer composition to absorb water, which can help stabilize the dielectric constant at high frequency ranges. Namely, such high naphthenic polymers typically have a water adsorption of about 0.015% or less, in some embodiments about 0.01% or less, and in some embodiments, from about 0.0001% to about 0.008% after being immersed in water for 24 hours in accordance with ISO 62-1:2008. The high naphthenic polymers may also have a moisture adsorption of about 0.01% or less, in some embodiments about 0.008% or less, and in some embodiments, from about 0.0001% to about 0.006% after being exposed to a humid atmosphere (50% relative humidity) at a temperature of 23° C. in accordance with ISO 62-4:2008.

In one embodiment, for instance, the repeating units derived from HNA may constitute 30 mol. % or more, in some embodiments about 40 mol. % or more, in some embodiments about 45 mol. % or more, in some embodiments 50 mol. % or more, in some embodiments about 55 mol. % or more, and in some embodiments, from about 55 mol. % to about 95 mol. % of the polymer. In such embodiments, the liquid crystalline polymer may contain various other monomers, such as aromatic hydroxycarboxylic acid(s) (e.g., HBA) in an amount of from about 1 mol. % to about 50 mol. %, and in some embodiments from about 1 mol. % to about 20 mol. %, and in some embodiments, from about 2 mol. % to about 10 mol. %; aromatic dicarboxylic acid(s) (e.g., IA and/or TA) in an amount of from about 1 mol. % to about 40 mol. %, and in some embodiments, from about 5 mol. % to about 25 mol. %; and/or aromatic diol(s) (e.g., BP and/or HQ) in an amount of from about 1 mol. % to about 40 mol. %, and in some embodiments, from about 5 mol. % to about 25 mol. %. In another embodiment, the repeating units derived from NDA may constitute 10 mol. % or more, in some embodiments about 12 mol. % or more, in some embodiments about 15 mol. % or more, and in some embodiments, from about 18 mol. % to about 95 mol. % of the polymer. In such embodiments, the liquid crystalline polymer may also contain various other monomers, such as aromatic hydroxycarboxylic acid(s) (e.g., HBA) in an amount of from about 20 mol. % to about 60 mol. %, and in some embodiments, from about 30 mol. % to about 50 mol. %; aromatic dicarboxylic acid(s) (e.g., IA and/or TA) in an amount of from about 2 mol. % to about 30 mol. %, and in some embodiments, from about 5 mol. % to about 25 mol. %; and/or aromatic diol(s) (e.g., BP and/or HQ) in an amount of from about 2 mol. % to about 40 mol. %, and in some embodiments, from about 5 mol. % to about 35 mol. %.

Of course, "low naphthenic" liquid crystalline polymers may also be employed in the composition, either alone or in combination with "high naphthenic" liquid crystalline polymers. In such low naphthenic polymers, the total amount of repeating units derived from naphthenic hydroxycarboxylic and/or dicarboxylic acids (e.g., NDA, HNA, or a combination of HNA and NDA) is typically less than 10 mol. %, in some embodiments about 8 mol. % or less, in some embodiments about 6 mol. % or less, and in some embodiments, from about 1 mol. % to about 5 mol. % of the polymer.

Regardless of the particular constituents and nature of the polymer, the liquid crystalline polymer may be prepared by initially introducing the aromatic monomer(s) used to form the ester repeating units (e.g., aromatic hydroxycarboxylic acid, aromatic dicarboxylic acid, etc.) and/or other repeating units (e.g., aromatic diol, aromatic amide, aromatic amine, etc.) into a reactor vessel to initiate a polycondensation reaction. The particular conditions and steps employed in such reactions are well known, and may be described in more detail in U.S. Pat. No. 4,161,470 to Calundann; U.S. Pat. No. 5,616,680 to Linstid, III, et al.; U.S. Pat. No. 6,114,492 to Linstid, III, et al.; U.S. Pat. No. 6,514,611 to Shepherd, et al.; and WO 2004/058851 to Waggoner. The vessel employed for the reaction is not especially limited, although it is typically desired to employ one that is commonly used in reactions of high viscosity fluids. Examples of such a reaction vessel may include a stirring tank-type apparatus that has an agitator with a variably-shaped stirring blade, such as an anchor type, multistage type, spiral-ribbon type, screw shaft type, etc., or a modified shape thereof. Further examples of such a reaction vessel may include a mixing apparatus commonly used in resin kneading, such as a kneader, a roll mill, a Banbury mixer, etc.

If desired, the reaction may proceed through the acetylation of the monomers as known the art. This may be accomplished by adding an acetylating agent (e.g., acetic anhydride) to the monomers. Acetylation is generally initiated at temperatures of about 90° C. During the initial stage of the acetylation, reflux may be employed to maintain vapor phase temperature below the point at which acetic acid byproduct and anhydride begin to distill. Temperatures during acetylation typically range from between 90° C. to 150° C., and in some embodiments, from about 110° C. to about 150° C. If reflux is used, the vapor phase temperature typically exceeds the boiling point of acetic acid, but remains low enough to retain residual acetic anhydride. For example, acetic anhydride vaporizes at temperatures of about 140° C. Thus, providing the reactor with a vapor phase reflux at a temperature of from about 110° C. to about 130° C. is particularly desirable. To ensure substantially complete reaction, an excess amount of acetic anhydride may be employed. The amount of excess anhydride will vary depending upon the particular acetylation conditions employed, including the presence or absence of reflux. The use of an excess of from about 1 to about 10 mole percent of acetic anhydride, based on the total moles of reactant hydroxyl groups present is not uncommon.

Acetylation may occur in in a separate reactor vessel, or it may occur in situ within the polymerization reactor vessel. When separate reactor vessels are employed, one or more of the monomers may be introduced to the acetylation reactor and subsequently transferred to the polymerization reactor. Likewise, one or more of the monomers may also be directly introduced to the reactor vessel without undergoing pre-acetylation.

In addition to the monomers and optional acetylating agents, other components may also be included within the reaction mixture to help facilitate polymerization. For instance, a catalyst may be optionally employed, such as metal salt catalysts (e.g., magnesium acetate, tin(I) acetate, tetrabutyl titanate, lead acetate, sodium acetate, potassium acetate, etc.) and organic compound catalysts (e.g., N-methylimidazole). Such catalysts are typically used in amounts of from about 50 to about 500 parts per million based on the total weight of the recurring unit precursors. When separate reactors are employed, it is typically desired to apply the catalyst to the acetylation reactor rather than the polymerization reactor, although this is by no means a requirement.

The reaction mixture is generally heated to an elevated temperature within the polymerization reactor vessel to initiate melt polycondensation of the reactants. Polycondensation may occur, for instance, within a temperature range of from about 250° C. to about 380° C., and in some embodiments, from about 280° C. to about 380° C. For instance, one suitable technique for forming the aromatic polyester may include charging precursor monomers and acetic anhydride into the reactor, heating the mixture to a temperature of from about 90° C. to about 150° C. to acetylize a hydroxyl group of the monomers (e.g., forming acetoxy), and then increasing the temperature to from about 280° C. to about 380° C. to carry out melt polycondensation. As the final polymerization temperatures are approached, volatile byproducts of the reaction (e.g., acetic acid) may also be removed so that the desired molecular weight may be readily achieved. The reaction mixture is generally subjected to agitation during polymerization to ensure good heat and mass transfer, and in turn, good material homogeneity. The rotational velocity of the agitator may vary during the course of the reaction, but typically ranges from about 10 to about 100 revolutions per minute ("rpm"), and in some embodiments, from about 20 to about 80 rpm. To build molecular weight in the melt, the polymerization reaction may also be conducted under vacuum, the application of which facilitates the removal of volatiles formed during the final stages of polycondensation. The vacuum may be created by the application of a suctional pressure, such as within the range of from about 5 to about 30 pounds per square inch ("psi"), and in some embodiments, from about 10 to about 20 psi.

Following melt polymerization, the molten polymer may be discharged from the reactor, typically through an extrusion orifice fitted with a die of desired configuration, cooled, and collected. Commonly, the melt is discharged through a perforated die to form strands that are taken up in a water bath, pelletized and dried. In some embodiments, the melt polymerized polymer may also be subjected to a subsequent solid-state polymerization method to further increase its molecular weight. Solid-state polymerization may be conducted in the presence of a gas (e.g., air, inert gas, etc.). Suitable inert gases may include, for instance, include nitrogen, helium, argon, neon, krypton, xenon, etc., as well as combinations thereof. The solid-state polymerization reactor vessel can be of virtually any design that will allow the polymer to be maintained at the desired solid-state polymerization temperature for the desired residence time. Examples of such vessels can be those that have a fixed bed, static bed, moving bed, fluidized bed, etc. The temperature at which solid-state polymerization is performed may vary, but is typically within a range of from about 250° C. to about 350° C. The polymerization time will of course vary based on the temperature and target molecular weight. In most cases, however, the solid-state polymerization time will be from about 2 to about 12 hours, and in some embodiments, from about 4 to about 10 hours.

B. Other Additives

In some cases, liquid crystalline polymers may constitute the entire polymer composition (e.g., 100 wt. %). Nevertheless, it may be desirable in certain embodiments to include one or more additives within the polymer composition to help achieve certain target properties. In such embodiments, the polymer composition typically contains one or more liquid crystalline polymers in an amount of from about 30 wt. % to about 99 wt. %, in some embodiments from about 40 wt. % to about 95 wt. %, and in some embodiments, from about 50 wt. % to about 90 wt. % of the entire polymer composition, as well as one or more additives in an amount of from about 1 wt. % to about 70 wt. %, in some embodiments from about 5 wt. % to about 60 wt. %, and in some embodiments, from about 10 wt. % to about 50 wt. % of the polymer composition. When employed, the particular nature of the additives may vary, such as described in more detail below.

i. Mineral Filler

In certain embodiments, the polymer composition may contain a mineral filler, which may be in the form of particles (e.g., platelet-shaped, flake-shaped, etc.), fibers (or "whiskers"), and so forth. Typically, the mineral filler has a certain hardness value to help improve the mechanical strength, adhesive strength, and surface properties of the composition, which enables the composition to be uniquely suited to form the small components of a medical device. For instance, the hardness values may be about 2.0 or more, in some embodiments about 2.5 or more, in some embodiments about 3.0 or more, in some embodiments from about 3.0 to about 11.0, in some embodiments from about 3.5 to about 11.0, and in some embodiments, from about 4.5 to about 6.5 based on the Mohs hardness scale. Any of a variety of different types of mineral particles may generally be employed, such as those formed from a natural and/or synthetic silicate mineral, such as talc, mica, halloysite, kaolinite, illite, montmorillonite, vermiculite, palygorskite, pyrophyllite, calcium silicate, aluminum silicate, wollastonite, etc.; sulfates; carbonates; phosphates; fluorides, borates; and so forth. Particularly suitable are particles having the desired hardness value, such as calcium carbonate ($CaCO_3$, Mohs hardness of 3.0), copper carbonate hydroxide ($Cu_2CO_3(OH)_2$, Mohs hardness of 4.0); calcium fluoride ($CaFl_2$, Mohs hardness of 4.0); calcium pyrophosphate (($Ca_2P_2O_7$, Mohs hardness of 5.0), anhydrous dicalcium phosphate ($CaHPO_4$, Mohs hardness of 3.5); hydrated aluminum phosphate ($AlPO_4 \cdot 2H_2O$, Mohs hardness of 4.5); potassium aluminum silicate ($KAlSi_3O_8$, Mohs hardness of 6), copper silicate ($CuSiO_3 \cdot H_2O$, Mohs hardness of 5.0); calcium borosilicate hydroxide ($Ca_2B_5SiO_9(OH)_5$, Mohs hardness of 3.5); calcium sulfate ($CaSO_4$, Mohs hardness of 3.5), barium sulfate ($BaSO_4$, Mohs hardness of from 3 to 3.5), mica (Mohs hardness of 2.5-5.3), and so forth, as well as combinations thereof. Mica, for instance, is particularly suitable. Any form of mica may generally be employed, including, for instance, muscovite ($KAl_2(AlSi_3)O_{10}(OH)_2$), biotite ($K(Mg,Fe)_3(AlSi_3)O_{10}(OH)_2$), phlogopite ($KMg_3(AlSi_3)O_{10}(OH)_2$), lepidolite ($K(Li,Al)_{2-3}(AlSi_3)O_{10}(OH)_2$), glauconite ($(K,Na)(Al,Mg,Fe)_2(Si,Al)_4O_{10}(OH)_2$), etc. Muscovite-based mica is particularly suitable for use in the polymer composition.

In certain embodiments, the mineral particles, such as barium sulfate and/or calcium sulfate particles, may have a shape that is generally granular or nodular in nature. In such embodiments, the particles may have a median size (e.g., diameter) of from about 0.5 to about 20 micrometers, in some embodiments from about 1 to about 15 micrometers, in some embodiments from about 1.5 to about 10 micrometers, and in some embodiments, from about 2 to about 8 micrometers, such as determined using laser diffraction techniques in accordance with ISO 13320:2020 (e.g., with a Horiba LA-960 particle size distribution analyzer). In other embodiments, it may also be desirable to employ flake-shaped mineral particles, such as mica particles, that have a relatively high aspect ratio (e.g., average diameter divided by average thickness), such as about 4 or more, in some embodiments about 8 or more, and in some embodiments, from about 10 to about 500. In such embodiments, the average diameter of the particles may, for example, range from about 5 micrometers to about 200 micrometers, in some embodiments from about 8 micrometers to about 150 micrometers, and in some embodiments, from about 10 micrometers to about 100 micrometers. The average thickness may likewise be about 2 micrometers or less, in some embodiments from about 5 nanometers to about 1 micrometer, and in some embodiments, from about 20 nanometers to about 500 nanometers such as determined using laser diffraction techniques in accordance with ISO 13320:2020 (e.g., with a Horiba LA-960 particle size distribution analyzer).

Suitable mineral fibers may likewise include those that are derived from silicates, such as neosilicates, sorosilicates, inosilicates (e.g., calcium inosilicates, such as wollastonite; calcium magnesium inosilicates, such as tremolite; calcium magnesium iron inosilicates, such as actinolite; magnesium iron inosilicates, such as anthophyllite; etc.), phyllosilicates (e.g., aluminum phyllosilicates, such as palygorskite), tectosilicates, etc.; sulfates, such as calcium sulfates (e.g., dehydrated or anhydrous gypsum); mineral wools (e.g., rock or slag wool); and so forth. Particularly suitable are fibers having the desired hardness value, including fibers derived from inosilicates, such as wollastonite (Mohs hardness of 4.5 to 5.0), which are commercially available from Nyco Minerals under the trade designation Nyglos® (e.g., Nyglos® 4 W or Nyglos® 8). The mineral fibers may have a median width (e.g., diameter) of from about 1 to about 35 micrometers, in some embodiments from about 2 to about 20 micrometers, in some embodiments from about 3 to about 15 micrometers, and in some embodiments, from about 7 to about 12 micrometers. In addition to possessing the size characteristics noted above, the mineral fibers may also have a relatively high aspect ratio (average length divided by median width) to help further improve the mechanical properties and surface quality of the resulting polymer composition. For example, the mineral fibers may have an aspect ratio of from about 2 to about 100, in some embodiments from about 2 to about 50, in some embodiments from about 3 to about 20, and in some embodiments, from about 4 to about 15. The volume average length of such mineral fibers may, for example, range from about 1 to about 200 micrometers, in some embodiments from about 2 to about 150 micrometers, in some embodiments from about 5 to about 100 micrometers, and in some embodiments, from about 10 to about 50 micrometers.

When employed, mineral fillers typically constitute from about 5 to about 150 parts, in some embodiments from about 20 to about 100 parts, and in some embodiments, from about 40 to about 80 parts by weight per 100 parts by weight of liquid crystalline polymers employed in the composition. For example, mineral fillers may constitute from about 5 wt. % to about 60 wt. %, in some embodiments from about 15 wt. % to about 55 wt. %, and in some embodiments, from about 25 wt. % to about 50 wt. % of the polymer composition.

ii. Electrically Conductive Filler

If desired, an electrically conductive filler may be employed so that the polymer composition is generally antistatic in nature. More particularly, the polymer composition may exhibit a controlled resistivity that allows it to remain generally antistatic in nature such that a substantial amount of electrical current does not flow through the part, but nevertheless exhibits a sufficient degree of electrostatic dissipation to facilitate the ability of the composition to be plated if so desired. The surface resistivity may, for instance, range from about $1 \times 10^{12}$ ohms to about $1 \times 10^{18}$ ohms, in some embodiments from about $1 \times 10^{13}$ ohms to about $1 \times 10^{18}$ ohms, in some embodiments from about $1 \times 10^{14}$ ohms to about $1 \times 10^{17}$ ohms, and in some embodiments, from about $1 \times 10^{15}$ ohms to about $1 \times 10^{17}$ ohms, such as determined in accordance with ASTM D257-14 (technically equivalent to IEC 62631-3-1). Likewise, the composition may also exhibit a volume resistivity of from about $1 \times 10^{10}$ ohm-m to about $1 \times 10^{16}$ ohm-m, in some embodiments from about $1 \times 10^{11}$ ohm-m to about $1 \times 10^{16}$ ohm-m, in some embodiments from about $1 \times 10^{12}$ ohm-m to about $1 \times 10^{15}$ ohm-m, and in some embodiments, from about $1 \times 10^{13}$ ohm-m to about $1 \times 10^{15}$ ohm-m, such as determined at a temperature of about 20° C. in accordance with ASTM D257-14 (technically equivalent to IEC 62631-3-1).

To achieve the desired degree of antistatic behavior, a single material may be selected having the desired resistivity, or multiple materials may be blended together (e.g., insulative and electrically conductive) so that the resulting filler has the desired resistivity. In one particular embodiment, for example, an electrically conductive material may be employed that has a volume resistivity of less than about 1 ohm-cm, in some embodiments about less than about 0.1 ohm-cm, and in some embodiments, from about $1 \times 10^{-8}$ ohm-cm to about $1 \times 10^{-2}$ ohm-cm, such as determined at a temperature of about 20° C. in accordance with ASTM D257-14 (technically equivalent to IEC 62631-3-1). Suitable electrically conductive carbon materials may include, for instance, graphite, carbon black, carbon fibers, graphene, carbon nanotubes, etc. Other suitable electrically conductive fillers may likewise include metals (e.g., metal particles, metal flakes, metal fibers, etc.), ionic liquids, and so forth. In one embodiment, for instance, the antistatic filler may be an ionic liquid. One benefit of such a material is that, in addition to being an antistatic agent, the ionic liquid can also exist in liquid form during melt processing, which allows it to be more uniformly blended within the polymer matrix. This improves electrical connectivity and thereby enhances the ability of the composition to rapidly dissipate static electric charges from its surface. The ionic liquid is generally a salt that has a low enough melting temperature so that it can be in the form of a liquid when melt processed with the liquid crystalline polymer. For example, the melting temperature of the ionic liquid may be about 400° C. or less, in some embodiments about 350° C. or less, in some embodiments from about 1° C. to about 100° C., and in some embodiments, from about 5° C. to about 50° C. The salt contains a cationic species and counterion. The cationic species contains a compound having at least one heteroatom (e.g., nitrogen or phosphorous) as a "cationic center." Examples of such heteroatomic compounds include, for instance, quaternary oniums having the following structures:

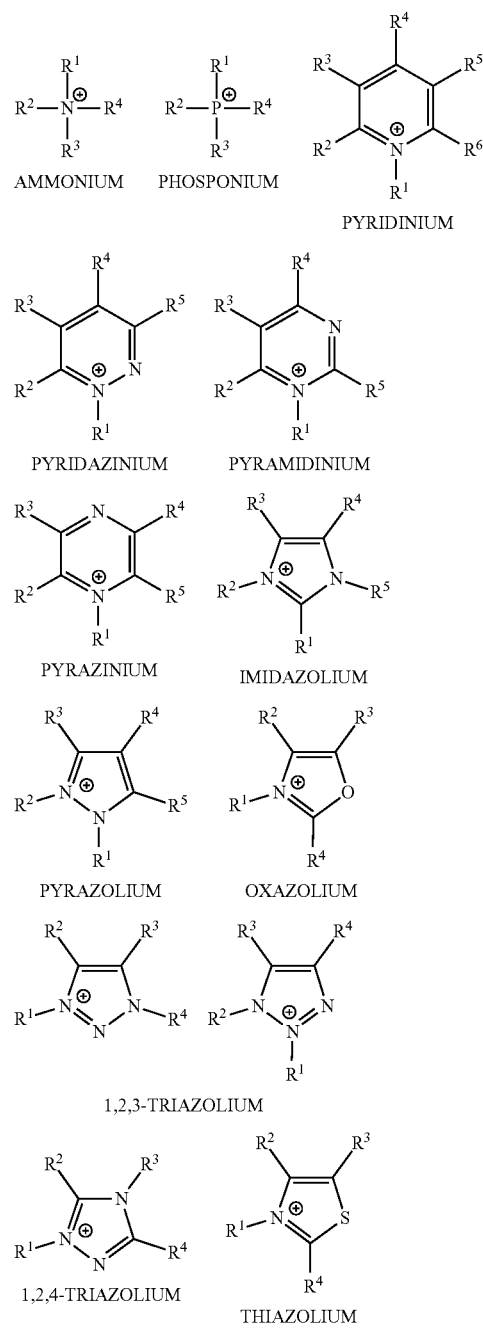

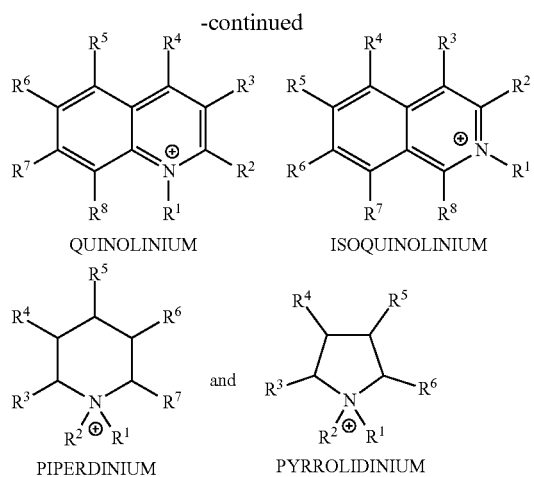

QUINOLINIUM    ISOQUINOLINIUM

PIPERDINIUM    PYRROLIDINIUM wherein, $R^1$, $R^2$, $R^3$, $R^4$, $R^5$, $R^6$, $R^7$, and $R^8$ are independently selected from the group consisting of hydrogen; substituted or unsubstituted $C_1$-$C_{10}$ alkyl groups (e.g., methyl, ethyl, n-propyl, isopropyl, n-butyl, isobutyl, sec-butyl, tert-butyl, n-pentyl, etc.); substituted or unsubstituted $C_3$-$C_{14}$ cycloalkyl groups (e.g., adamantyl, cyclopropyl, cyclobutyl, cyclopentyl, cyclooctyl, cyclohexenyl, etc.); substituted or unsubstituted $C_1$-$C_{10}$ alkenyl groups (e.g., ethylene, propylene, 2-methypropylene, pentylene, etc.); substituted or unsubstituted $C_2$-$C_{10}$ alkynyl groups (e.g., ethynyl, propynyl, etc.); substituted or unsubstituted $C_1$-$C_{10}$ alkoxy groups (e.g., methoxy, ethoxy, n-propoxy, isopropoxy, n-butoxy, t-butoxy, sec-butoxy, n-pentoxy, etc.); substituted or unsubstituted acyloxy groups (e.g., methacryloxy, methacryloxyethyl, etc.); substituted or unsubstituted aryl groups (e.g., phenyl); substituted or unsubstituted heteroaryl groups (e.g., pyridyl, furanyl, thienyl, thiazolyl, isothiazolyl, triazolyl, imidazolyl, isoxazolyl, pyrrolyl, pyrazolyl, pyridazinyl, pyrimidinyl, quinolyl, etc.); and so forth. In one particular embodiment, for example, the cationic species may be an ammonium compound having the structure $n^+r^1r^2r^3r^4$, wherein $r^1$, $r^2$, and/or $r^3$ are independently a $c_1$-$c_6$ alkyl (e.g., methyl, ethyl, butyl, etc.) and $R^4$ is hydrogen or a $C_1$-$C_4$ alkyl group (e.g., methyl or ethyl). For example, the cationic component may be tri-butylmethyl-ammonium, wherein $R^1$, $R^2$, and $R^3$ are butyl and $R^4$ is methyl.

Suitable counterions for the cationic species may include, for example, halogens (e.g., chloride, bromide, iodide, etc.); sulfates or sulfonates (e.g., methyl sulfate, ethyl sulfate, butyl sulfate, hexyl sulfate, octyl sulfate, hydrogen sulfate, methane sulfonate, dodecylbenzene sulfonate, dodecylsulfate, trifluoromethane sulfonate, heptadecafluorooctanesulfonate, sodium dodecylethoxysulfate, etc.); sulfosuccinates; amides (e.g., dicyanamide); imides (e.g., bis(pentafluoroethyl-sulfonyl)imide, bis(trifluoromethylsulfonyl)imide, bis(trifluoromethyl)imide, etc.); borates (e.g., tetrafluoroborate, tetracyanoborate, bis[oxalato]borate, bis[salicylato]borate, etc.); phosphates or phosphinates (e.g., hexafluorophosphate, diethylphosphate, bis(pentafluoroethyl)phosphinate, tris(pentafluoroethyl)-trifluorophosphate, tris(nonafluorobutyl)trifluorophosphate, etc.); antimonates (e.g., hexafluoroantimonate); aluminates (e.g., tetrachloroaluminate); fatty acid carboxylates (e.g., oleate, isostearate, pentadecafluorooctanoate, etc.); cyanates; acetates; and so forth, as well as combinations of any of the foregoing. To help improve compatibility with the liquid crystalline polymer, it may be desired to select a counterion that is generally hydrophobic in nature, such as imides, fatty acid carboxylates, etc. Particularly suitable hydrophobic counterions may include, for instance, bis (pentafluoroethylsulfonyl)imide, bis(trifluoromethylsulfonyl)imide, and bis(trifluoromethyl)imide.

When employed, electrically conductive fillers typically constitute from about 0.5 to about 20 parts, in some embodiments from about 1 to about 15 parts, and in some embodiments, from about 2 to about 8 parts by weight per 100 parts by weight of liquid crystalline polymers employed in the composition. For example, electrically conductive fillers may constitute from about 0.1 wt. % to about 10 wt. %, in some embodiments from about 0.2 wt. % to about 8 wt. %, and in some embodiments, from about 0.5 wt. % to about 4 wt. % of the polymer composition.

iii. Impact Modifier

An impact modifier may also be employed in the polymer composition. For example, the impact modifier may be a polymer that contains an olefinic monomeric unit that derived from one or more α-olefins. Examples of such monomers include, for instance, linear and/or branched α-olefins having from 2 to 20 carbon atoms and typically from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin monomers are ethylene and propylene. The olefin polymer may be in the form of a copolymer that contains other monomeric units as known in the art. For example, another suitable monomer may include a "(meth)acrylic" monomer, which includes acrylic and methacrylic monomers, as well as salts or esters thereof, such as acrylate and methacrylate monomers. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof. In one embodiment, for instance, the impact modifier may be an ethylene methacrylic acid copolymer ("EMAC"). When employed, the relative portion of the monomeric component(s) may be selectively controlled. The α-olefin monomer(s) may, for instance, constitute from about 55 wt. % to about 95 wt. %, in some embodiments from about 60 wt. % to about 90 wt. %, and in some embodiments, from about 65 wt. % to about 85 wt. % of the copolymer. Other monomeric components (e.g., (meth)acrylic monomers) may constitute from about 5 wt. % to about 35 wt. %, in some embodiments from about 10 wt. % to about 32 wt. %, and in some embodiments, from about 15 wt. % to about 30 wt. % of the copolymer.

Other suitable olefin copolymers may be those that are "epoxy-functionalized" in that they contain, on average, two or more epoxy functional groups per molecule. The copolymer may also contain an epoxy-functional monomeric unit. One example of such a unit is an epoxy-functional (meth)acrylic monomeric component. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethylacrylate, and glycidyl itaconate. Other suitable monomers may also be employed to help achieve the desired molecular weight. In one particular embodiment, for example, the copolymer may be a terpolymer formed from an epoxy-functional (meth)acrylic monomeric component, α-olefin monomeric component, and non-epoxy functional (meth)acrylic monomeric component. The copolymer may, for instance, be poly(ethylene-co-butylacrylate-co-glycidyl methacrylate). When employed, the epoxy-functional (meth)acrylic monomer(s) typically constitutes from about 1 wt. % to about 20 wt. %, in some embodiments from about 2 wt. % to about 15 wt. %, and in some embodiments, from about 3 wt. % to about 10 wt. % of the copolymer.

When employed, impact modifiers typically constitute from about 0.5 to about 60 parts, in some embodiments from about 1 to about 50 parts, and in some embodiments, from about 2 to about 30 parts by weight per 100 parts by weight of the liquid crystalline polymers employed in the composition. For example, impact modifiers may constitute from about 0.1 wt. % to about 30 wt. %, in some embodiments from about 0.5 wt. % to about 25 wt. %, and in some embodiments, from about 1 wt. % to about 20 wt. % of the polymer composition.

iv. Laser Activatable Additive

In some embodiments, the polymer composition may be "laser activatable" in the sense that it contains an additive that can be activated by a laser direct structuring ("LDS") process to form conductive elements (e.g., antenna elements) thereon. In such a process, the additive is exposed to a laser that causes the release of metals. The laser thus draws the pattern of conductive elements onto the part and leaves behind a roughened surface containing embedded metal particles. These particles act as nuclei for the crystal growth during a subsequent plating process (e.g., copper plating, gold plating, nickel plating, silver plating, zinc plating, tin plating, etc.). When employed, laser activatable additives typically constitute from about 0.1 wt. % to about 30 wt. %, in some embodiments from about 0.5 wt. % to about 20 wt. %, and in some embodiments, from about 1 wt. % to about 10 wt. % of the polymer composition. The laser activatable additive generally includes spinel crystals, which may include two or more metal oxide cluster configurations within a definable crystal formation. For example, the overall crystal formation may have the following general formula:

$$AB_2O_4$$

wherein,
A is a metal cation having a valance of 2, such as cadmium, chromium, manganese, nickel, zinc, copper, cobalt, iron, magnesium, tin, titanium, etc., as well as combinations thereof; and
B is a metal cation having a valance of 3, such as chromium, iron, aluminum, nickel, manganese, tin, etc., as well as combinations thereof.

Typically, A in the formula above provides the primary cation component of a first metal oxide cluster and B provides the primary cation component of a second metal oxide cluster. These oxide clusters may have the same or different structures. In one embodiment, for example, the first metal oxide cluster has a tetrahedral structure and the second metal oxide cluster has an octahedral cluster. Regardless, the clusters may together provide a singular identifiable crystal type structure having heightened susceptibility to electromagnetic radiation. Examples of suitable spinel crystals include, for instance, $MgAl_2O_4$, $ZnAl_2O_4$, $FeAl_2O_4$, $CuFe_2O_4$, $CuCr_2O_4$, $MnFe_2O_4$, $NiFe_2O_4$, $TiFe_2O_4$, $FeCr_2O_4$, $MgCr_2O_4$, etc. Copper chromium oxide ($CuCr_2O_4$) is particularly suitable for use in the present invention and is available from Shepherd Color Co. under the designation "Shepherd Black 1GM."

v. Hydrophobic Material

If desired, an additional hydrophobic material may be employed in the polymer composition to help further reduce its tendency to absorb water, which can help stabilize the dielectric constant and dissipation factor at high frequency ranges. When employed, the weight ratio of liquid crystalline polymer(s) to hydrophobic material(s) is typically from about 1 to about 20, in some embodiments from about 2 to about 15, and in some embodiments, from about 3 to about 10. For example, the hydrophobic material may constitute from about 1 wt. % to about 60 wt. %, in some embodiments from about 2 wt. % to about 50 wt. %, and in some embodiments, from about 5 wt. % to about 40 wt. % of the entire polymer composition.

Particularly suitable hydrophobic materials are low surface energy elastomers, such as fluoropolymers, silicone polymers, etc. Fluoropolymers, for instance, may contains a hydrocarbon backbone polymer in which some or all of the hydrogen atoms are substituted with fluorine atoms. The backbone polymer may be polyolefinic and formed from fluorine-substituted, unsaturated olefin monomers. The fluoropolymer can be a homopolymer of such fluorine-substituted monomers or a copolymer of fluorine-substituted monomers or mixtures of fluorine-substituted monomers and non-fluorine-substituted monomers. Along with fluorine atoms, the fluoropolymer can also be substituted with other halogen atoms, such as chlorine and bromine atoms. Representative monomers suitable for forming fluoropolymers for use in this invention are tetrafluoroethylene ("TFE"), vinylidene fluoride ("VF2"), hexafluoropropylene ("HFP"), chlorotrifluoroethylene ("CTFE"), perfluoroethylvinyl ether ("PEVE"), perfluoromethylvinyl ether ("PMVE"), perfluoropropylvinyl ether ("PPVE"), etc., as well as mixtures thereof. Specific examples of suitable fluoropolymers include polytetrafluoroethylene ("PTFE"), perfluoroalkylvinyl ether ("PVE"), poly(tetrafluoroethylene-co-perfluoroalkyvinyl ether) ("PFA"), fluorinated ethylene-propylene copolymer ("FEP"), ethylene-tetrafluoroethylene copolymer ("ETFE"), polyvinylidene fluoride ("PVDF"), polychlorotrifluoroethylene ("PCTFE"), and TFE copolymers with VF2 and/or HFP, etc., as well as mixtures thereof.

In certain embodiments, the hydrophobic material (e.g., fluoropolymer) may have a particle size that is selectively controlled to help form films of a relatively low thickness. For example, the hydrophobic material may have a median particle size (e.g., diameter) of about 1 to about 60 micrometers, in some embodiments from about 2 to about 55 micrometers, in some embodiments from about 3 to about 50 micrometers, and in some embodiments, from about 25 to about 50 micrometers, such as determined using laser diffraction techniques in accordance with ISO 13320:2009 (e.g., with a Horiba LA-960 particle size distribution analyzer). The hydrophobic material may also have a narrow size distribution. That is, at least about 70% by volume of the particles, in some embodiments at least about 80% by volume of the particles, and in some embodiments, at least about 90% by volume of the particles may have a size within the ranges noted above.

vi. Hollow Filler

Although by no means required, the polymer composition may also include one or more hollow inorganic fillers to help achieve the desired dielectric constant. For instance, such fillers may have a dielectric constant of about 3.0 or less, in some embodiments about 2.5 or less, in some embodiments from about 1.1 to about 2.3, and in some embodiments from about 1.2 to about 2.0 at 100 MHz. The hollow inorganic fillers typically have an interior hollow space or cavity and may be synthesized using techniques known in the art. The hollow inorganic fillers may be made from conventional materials. For instance, the hollow inorganic fillers may include alumina, silica, zirconia, magnesia, glass, fly ash, borate, phosphate, ceramic, and the like. In one embodiment, the hollow inorganic fillers may include hollow glass fillers, hollow ceramic fillers, and mixtures thereof. In one embodiment, the hollow inorganic fillers include hollow glass fillers. The hollow glass fillers may be made from a soda lime borosilicate glass, a soda lime glass, a borosilicate glass, a sodium borosilicate glass, a sodium silicate glass, or an aluminosilicate glass. In this regard, in one embodiment, the composition of the glass, while not limited, may be at least about 65% by weight of $SiO_2$, 3-15% by weight of $Na_2O$, 8-15% by weight of CaO, 0.1-5% by weight of MgO, 0.01-3% by weight of $Al_2O_3$, 0.01-1% by weight of $K_2O$, and optionally other oxides (e.g., $Li_2O$, $Fe_2O_3$, $TiO_2$, $B_2O_3$). In another embodiment, the composition may be about 50-58% by weight of $SiO_2$, 25-30% by weight of $Al_2O_3$, 6-10% by weight of CaO, 1-4% by weight of $Na_2O/K_2O$, and 1-5% by weight of other oxides. Also, in one embodiment, the hollow glass fillers may include more alkaline earth metal oxides than alkali metal oxides. For example, the weight ratio of the alkaline earth metal oxides to the alkali metal oxides may be more than 1, in some embodiments about 1.1 or more, in some embodiments about 1.2 to about 4, and in some embodiments from about 1.5 to about 3. Regardless of the above, it should be understood that the glass composition may vary depending on the type of glass utilized and still provide the benefits as desired by the present invention.

The hollow inorganic fillers may have at least one dimension having an average value that is about 1 micrometers or more, in some embodiments about 5 micrometers or more, in some embodiments about 8 micrometers or more, in some embodiments from about 1 micrometer to about 150 micrometers, in some embodiments from about 10 micrometers to about 150 micrometers, and in some embodiments from about 12 micrometers to about 50 micrometers. In one embodiment, such average value may refer to a $d_{50}$ value. Furthermore, the hollow inorganic fillers may have a $D_{10}$ of about 3 micrometers or more, in some embodiments about 4 micrometers or more, in some embodiments from about 5 micrometers to about 20 micrometers, and in some embodiments from about 6 micrometers to about 15 micrometers. The hollow inorganic fillers may have a $D_{90}$ of about 10 micrometers or more, in some embodiments about 15 micrometers or more, in some embodiments from about 20 micrometers to about 150 micrometers, and in some embodiments from about 22 micrometers to about 50 micrometers. In this regard, the hollow inorganic fillers may be present in a size distribution, which may be a Gaussian, normal, or non-normal size distribution. In one embodiment, the hollow inorganic fillers may have a Gaussian size distribution. In another embodiment, the hollow inorganic fillers may have a normal size distribution. In a further embodiment, the hollow inorganic fillers may have a non-normal size distribution. Examples of non-normal size distributions may include unimodal and multi-modal (e.g., bimodal) size distributions. When referring to dimensions above, such dimension may be any dimension. In one embodiment, however, such dimension refers to a diameter. For example, such value for the dimension refers to an average diameter of spheres. The dimension, such as the average diameter, may be determined in accordance to 3M QCM 193.0. In this regard, in one embodiment, the hollow inorganic fillers may be referring to hollow spheres such as hollow glass spheres. For instance, the hollow inorganic fillers may have an average aspect ratio of approximately 1. In general, the average aspect ratio may be about 0.8 or more, in some embodiments about 0.85 or more, in some embodiments from about 0.9 to about 1.3, and in some embodiments from about 0.95 to about 1.05.

In addition, the hollow inorganic fillers may have relatively thin walls to help with the dielectric properties of the polymer composition as well as the reduction in weight. The thickness of the wall may be about 50% or less, in some embodiments about 40% or less, in some embodiments from about 1% to about 30%, and in some embodiments from about 2% to about 25% the average dimension, such as the average diameter, of the hollow inorganic fillers. In addition, the hollow inorganic fillers may have a certain true density that can allow for easy handling and provide a polymer composition having a reduction in weight. In general, the true density refers to the quotient obtained by dividing the mass of a sample of the hollow fillers by the true volume of that mass of hollow fillers wherein the true volume is referred to as the aggregate total volume of the hollow fillers. In this regard, the true density of the hollow inorganic fillers may be about 0.1 $g/cm^3$ or more, in some embodiments about 0.2 $g/cm^3$ or more, in some embodiments from about 0.3 $g/cm^3$ or more to about 1.2 $g/cm^3$, and in some embodiments from about 0.4 $g/cm^3$ or more to about 0.9 $g/cm^3$. The true density may be determined in accordance to 3M QCM 14.24.1.

Even though the fillers are hollow, they may have a mechanical strength that allows for maintaining the integrity of the structure of the fillers resulting in a lower likelihood of the fillers being broken during processing and/or use. In this regard, the isotactic crush resistance (i.e., wherein at least 80 vol. %, such as at least 90 vol. % of the hollow fillers survive) of the hollow inorganic fillers may be about 20 MPa or more, in some embodiments about 100 MPa or more, in some embodiments from about 150 MPa to about 500 MPa, and in some embodiments from about 200 MPa to about 350 MPa. The isotactic crush resistance may be determined in accordance to 3M QCM 14.1.8.

The alkalinity of the hollow inorganic fillers may be about 1.0 meq/g or less, in some embodiments about 0.9 meq/g or less, in some embodiments from about 0.1 meq/g to about 0.8 meq/g, and in some embodiments from about 0.2 meq/g to about 0.7 meq/g. The alkalinity may be determined in accordance to 3M QCM 55.19. In order to provide a relatively low alkalinity, the hollow inorganic fillers may be treated with a suitable acid, such as a phosphoric acid. In addition, the hollow inorganic fillers may also include a surface treatment to assist with providing a better compatibility with the polymer and/or other components within the polymer composition. As an example, the surface treatment may be a silanization. In particular, the surface treatment agents may include, but are not limited to, aminosilanes, epoxysilanes, etc.

When employed, the hollow inorganic fillers may, for instance, constitute about 1 wt. % or more, in some embodiments about 4 wt. % or more, in some embodiments from about 5 wt. % to about 40 wt. %, and in some embodiments from about 10 wt. % to about 30 wt. % of the polymer composition.

vii. Other Additives

A wide variety of additional additives can also be included in the polymer composition, such as fibers (e.g., glass fibers), lubricants, thermally conductive fillers, pigments, antioxidants, stabilizers, surfactants, waxes, flame retardants, anti-drip additives, nucleating agents (e.g., boron nitride) and other materials added to enhance properties and processability. Lubricants, for example, may be employed in the polymer composition that are capable of withstanding the processing conditions of the liquid crystalline polymer without substantial decomposition. Examples of such lubricants include fatty acids esters, the salts thereof, esters, fatty acid amides, organic phosphate esters, and hydrocarbon waxes of the type commonly used as lubricants in the processing of engineering plastic materials, including mixtures thereof. Suitable fatty acids typically have a backbone carbon chain of from about 12 to about 60 carbon atoms, such as myristic acid, palmitic acid, stearic acid, arachic acid, montanic acid, octadecinic acid, parinric acid, and so forth. Suitable esters include fatty acid esters, fatty alcohol esters, wax esters, glycerol esters, glycol esters and complex esters. Fatty acid amides include fatty primary amides, fatty secondary amides, methylene and ethylene bisamides and alkanolamides such as, for example, palmitic acid amide, stearic acid amide, oleic acid amide, N,N'-ethylenebisstearamide and so forth. Also suitable are the metal salts of fatty acids such as calcium stearate, zinc stearate, magnesium stearate, and so forth; hydrocarbon waxes, including paraffin waxes, polyolefin and oxidized polyolefin waxes, and microcrystalline waxes. Particularly suitable lubricants are acids, salts, or amides of stearic acid, such as pentaerythritol tetrastearate, calcium stearate, or N,N'-ethylenebisstearamide. When employed, the lubricant(s) typically constitute from about 0.05 wt. % to about 1.5 wt. %, and in some embodiments, from about 0.1 wt. % to about 0.5 wt. % (by weight) of the polymer composition.

II. Formation

The ingredients used to form the polymer composition may be combined together using any of a variety of different techniques as is known in the art. In one particular embodiment, for example, the liquid crystalline polymer and other optional additives are melt processed as a mixture within an extruder to form the polymer composition. The mixture may be melt-kneaded in a single-screw or multi-screw extruder at a temperature of from about 200° C. to about 450° C. In one embodiment, the mixture may be melt processed in an extruder that includes multiple temperature zones. The temperature of individual zones is typically set within about −60° C. to about 25° C. relative to the melting temperature of the polymer. By way of example, the mixture may be melt processed using a twin screw extruder such as a Leistritz 18-mm co-rotating fully intermeshing twin screw extruder. A general purpose screw design can be used to melt process the mixture. In one embodiment, the mixture including all of the components may be fed to the feed throat in the first barrel by means of a volumetric feeder. In another embodiment, different components may be added at different addition points in the extruder, as is known. For example, the polymer may be applied at the feed throat, and certain additives (e.g., particulate filler) may be supplied at the same or different temperature zone located downstream therefrom. Regardless, the resulting mixture can be melted and mixed then extruded through a die. The extruded polymer composition can then be quenched in a water bath to solidify and granulated in a pelletizer followed by drying.

III. Component

As will be described in more detail below, the polymer composition may be used to form one or more components of the medical device. Due in part to the beneficial properties of the polymer composition, the component may have a very small size, such as a thickness of about 5 millimeters or less, in some embodiments about 4 millimeters or less, in some embodiments from about 0.1 to about 3.5 millimeters, and in some embodiments, from about 0.5 to about 3 millimeters. Regardless of the specific component in which it is employed, the polymer composition is generally shaped into the desired component using a variety of different techniques. Suitable techniques may include, for instance, film extrusion, thermoforming, injection molding, low-pressure injection molding, extrusion compression molding, gas injection molding, foam injection molding, low-pressure gas injection molding, low-pressure foam injection molding, gas extrusion compression molding, foam extrusion compression molding, extrusion molding, foam extrusion molding, compression molding, foam compression molding, gas compression molding, etc. For example, an injection molding system may be employed that includes a mold within which the polymer composition may be injected. The time inside the injector may be controlled and optimized so that polymer matrix is not pre-solidified. When the cycle time is reached and the barrel is full for discharge, a piston may be used to inject the composition to the mold cavity. Compression molding systems may also be employed. As with injection molding, the shaping of the polymer composition into the desired article also occurs within a mold. The composition may be placed into the compression mold using any known technique, such as by being picked up by an automated robot arm. The temperature of the mold may be maintained at or above the solidification temperature of the polymer composition for a desired time period to allow for solidification. The molded product may then be solidified by bringing it to a temperature below that of the melting temperature. The resulting product may be de-molded. The cycle time for each molding process may be adjusted to suit the polymer composition, to achieve sufficient bonding, and to enhance overall process productivity.

Depending on the manner in which it is used in the medical device (e.g., antenna element), it may also be desired to deposit one or more conductive elements on the component using any of a variety of known metal deposition techniques, such as plating (e.g., electrolytic plating, electroless plating, etc.), printing (e.g., digital printing, aerosol jet printing, etc.), and so forth. The conductive elements may contain one or more of a variety of conductive materials, such as a metal, e.g., gold, silver, nickel, aluminum, copper, as well as mixture or alloys thereof. In one embodiment, for instance, the conductive elements may include copper and/or nickel (e.g., pure or alloys thereof). If desired, a seed layer may initially be formed on the substrate to facilitate the metal deposition process.

When plating is employed as a deposition technique, the process may vary as desired. In certain embodiments, for instance, the process may include initially forming a pattern on the surface of the molded part based on the desired circuit interconnect pattern. This may be accomplished using various known techniques, such as laser ablation or patterning, plasma etching, ultraviolet light treatment, acid etching, etc. Regardless, after forming the desired pattern on the molded part, the patterned regions may then optionally be subjected to an activation process to prepare for subsequent metal deposition. During this process, the patterned component may be contacted with an activation solution that contains a metal, such as palladium, platinum, iridium, rhodium, etc., as well as mixtures thereof. Palladium is particularly suitable. Once the surface has been conditioned as described above, a first metal layer may then be formed thereon on the patterned component, such as through a process known as electroless plating. Electroless plating may occur through auto-catalytic reactions in which the metal deposited on the surface acts as a catalyst for further depositing. Typically, nickel and/or copper are electrolessly plated onto the surface of the patterned substrate. Electroless nickel plating may be accomplished, for example, using a solution that contains a nickel salt (e.g., nickel sulfate). If desired, the patterned component may also be subjected to one or more additional steps to form the final metal coating layer(s). Additional coating layer(s) are typically deposited using a process known as electrolytic plating, during which the patterned substrate is contacted with a metal solution and subjected to an electrical current to initiate deposition of the metal. For example, a second metal layer may be electrolytically deposited over the first metal layer (e.g., electrolessly plated copper and/or nickel). The second metal layer may include, for instance, copper or nickel. In certain embodiments, one or more additional metal layer(s), such as copper and/or nickel, may also be electrolytically deposited over the second metal layer.

IV. Medical Device and Wireless Communication System

As indicated above, the polymer composition of the present invention is employed in a medical device, such as a sensor configured to obtain physiological information (e.g., heart rate, oxygen saturation, chemicals in blood or subcutaneous interstitial fluid (e.g., glucose), body temperature, tissue hydration, etc., e.g., a wearable or implantable device; drug delivery device, such as an injection pen, autoinjector, infusion pump, subcutaneous injection pump, meter dose inhaler, dry powder inhaler, nasal inhaler, iontophoresis patch, etc.; telemetric device, such as home health or hospital monitors, CPAP machines, oxygen concentrators, medicine distribution containers, blood pressure cuffs, etc.; and so forth. The polymer composition may form only a portion of the component, or alternatively the entire component. Examples of components that may employ the polymer composition include, for instance, housing for the entire device and/or or a component thereof, one or more portions of any antenna system (e.g., substrate, window, repeater, etc.), radiofrequency filter, electrical connector, and so forth.

The medical device is generally configured to transmit and/or receive radiofrequency signals at a variety of frequencies, including Wireless Medical Telemetry Service (WMTS), Bluetooth, LTE, and 5G frequencies. In this manner, a wireless communication system may be employed that contains the medical device and an external device (e.g., desktop computer, portable electronic device (e.g., laptop, tablet, phone, etc.), wearable device (e.g., smartwatch), etc.). The information/data obtained by the medical device can be provided to the external device, which may be present at a local or remote location (e.g., doctor's office, hospital, etc.). Control signals from the external device may be received and processed by the medical device. To help facilitate the transmission of information/data, the wireless communication system may also contain an antenna system. The antenna system may be separate from and/or integrated within the medical device. For example, the medical device may contain a circuit structure that includes a substrate on which is disposed on or more antenna elements. If desired, the substrate may be formed from the polymer composition of the present invention and may be part of the medical device itself. The circuit structure may be configured to transmit and/or receive radiofrequency signals at a variety of frequencies as noted above. For example, the circuit structure may be particularly well suited for 5G systems. As used herein, "5G" generally refers to high speed data communication over radiofrequency signals. 5G networks and systems are capable of communicating data at much faster rates than previous generations of data communication standards (e.g., "4G", "LTE"). For example, as used herein, "5G frequencies" can refer to frequencies that are 1.5 GHz or more, in some embodiments about 2.0 GHz or more, in some embodiments about 2.5 GHz or higher, in some embodiments about 3.0 GHz or higher, in some embodiments from about 3 GHz to about 300 GHz, or higher, in some embodiments from about 4 GHz to about 80 GHz, in some embodiments from about 5 GHz to about 80 GHz, in some embodiments from about 20 GHz to about 80 GHz, and in some embodiments from about 28 GHz to about 60 GHz. Various standards and specifications have been released quantifying the requirements of 5G communications. As one example, the International Telecommunications Union (ITU) released the International Mobile Telecommunications-2020 ("IMT-2020") standard in 2015. The IMT-2020 standard specifies various data transmission criteria (e.g., downlink and uplink data rate, latency, etc.) for 5G. The IMT-2020 Standard defines uplink and downlink peak data rates as the minimum data rates for uploading and downloading data that a 5G system must support. The IMT-2020 standard sets the downlink peak data rate requirement as 20 Gbit/s and the uplink peak data rate as 10 Gbit/s. As another example, $3^{rd}$ Generation Partnership Project (3GPP) recently released new standards for 5G, referred to as "5G NR." 3GPP published "Release 15" in 2018 defining "Phase 1" for standardization of 5G NR. 3GPP defines 5G frequency bands generally as "Frequency Range 1" (FR1) including sub-6 GHz frequencies and "Frequency Range 2" (FR2) as frequency bands ranging from 20-60 GHz. Antenna systems described herein can satisfy or qualify as "5G" under standards released by 3GPP, such as Release 15 (2018), and/or the IMT-2020 Standard.

To achieve high speed data communication at high frequencies, antenna elements and arrays may employ small feature sizes/spacing (e.g., fine pitch technology) that can improve antenna performance. For example, the feature size (spacing between antenna elements, width of antenna elements) etc. is generally dependent on the wavelength ("$\lambda$") of the desired transmission and/or reception radiofrequency propagating through the substrate dielectric on which the antenna element is formed (e.g., $n\lambda/4$ where n is an integer and $\lambda$ is dependent on the dielectric constant of the substrate). Further, beamforming and/or beam steering can be employed to facilitate receiving and transmitting across multiple frequency ranges or channels (e.g., multiple-in-multiple-out (MIMO), massive MIMO). The high frequency 5G antenna elements can have a variety of configurations. For example, the 5G antenna elements can be or include co-planar waveguide elements, patch arrays (e.g., mesh-grid patch arrays), other suitable 5G antenna configurations. The antenna elements can be configured to provide MIMO, massive MIMO functionality, beam steering, and the like. As used herein "massive" MIMO functionality generally refers to providing a large number transmission and receiving channels with an antenna array achieved by frequency domain and/or time domain multiplexing, for example 8 transmission (Tx) and 8 receive (Rx) channels (abbreviated as 8×8). Massive MIMO functionality may be provided with 8×8, 12×12, 16×16, 32×32, 64×64, or greater.

The antenna elements can have a variety of configurations and arrangements and can be fabricated using a variety of manufacturing techniques. As one example, the antenna elements and/or associated elements (e.g., ground elements, feed lines, etc.) can employ fine pitch technology. Fine pitch technology generally refers to small or fine spacing between their components or leads. For example, feature dimensions and/or spacing between antenna elements (or between an antenna element and a ground plane) can be about 1,500 micrometers or less, in some embodiments 1,250 micrometers or less, in some embodiments 750 micrometers or less (e.g., center-to-center spacing of 1.5 mm or less), 650 micrometers or less, in some embodiments 550 micrometers or less, in some embodiments 450 micrometers or less, in some embodiments 350 micrometers or less, in some embodiments 250 micrometers or less, in some embodiments 150 micrometers or less, in some embodiments 100 micrometers or less, and in some embodiments 50 micrometers or less. However, it should be understood that feature sizes and/or spacings that are smaller and/or larger may be employed within the scope of this disclosure. As a result of such small feature dimensions, antenna systems can be achieved with a large number of antenna elements in a small footprint. For example, an antenna array can have an average antenna element concentration of greater than 1,000 antenna elements per square centimeter, in some embodiments greater than 2,000 antenna elements per square centimeter, in some embodiments greater than 3,000 antenna elements per square centimeter, in some embodiments greater than 4,000 antenna elements per square centimeter, in some embodiments greater than 6,000 antenna elements per square centimeter, and in some embodiments greater than about 8,000 antenna elements per square centimeter. Such compact arrangement of antenna elements can provide a greater number of channels for MIMO functionality per unit area of the antenna area. For example, the number of channels can correspond with (e.g., be equal to or proportional with) the number of antenna elements.

Apart from being employed in an antenna system, the polymer composition may also be employed in various other components of the medical device. For example, the medical device may include a housing that encloses one or more electrical elements, such as a printed circuit board, sensing circuitry, etc.; one or more medical elements, such as a drug reservoir, fluidic channels, etc.; and so forth. In one particular embodiment, for example, the medical device may be a sensor, such as a glucose monitor. In such embodiments, the sensor may contain a housing that encloses a printed circuit board ("PCB") that includes sensing circuitry that is connected to a chemical sensor (e.g., glucose) that penetrates a patient's skin and senses glucose concentration in the patient's interstitial fluid. The sensing circuitry is also connected to an antenna, which may be disposed on a surface of the housing to allow the glucose monitor to transmit sensor information to an external computing device, such as a tablet, computer, or smartphone. To help reduce signal loss, the polymer composition may be used to form all or a portion of the housing, insulative portion(s) of the printed circuit board, sensing circuitry, antenna, etc., as well as other components of the sensor.

Referring to FIG. 1, for example, one embodiment of a glucose monitor 100 is shown in more detail. The glucose monitor 100 may be a biomedical device for measuring biological parameters of a patient, such as a diabetic patient's glucose levels. The glucose monitor 100 may be a wearable device attached to a patient's skin 102, such as by an adhesive layer on a surface of the housing. In some aspects, the glucose monitor 100 may include one or more invasive or non-invasive sensor devices for measuring a patient's biological parameters and may use a transceiver coupled to an antenna positioned on the housing of the monitor 100 to communicate the parameter measurements to an external device 104. The antenna may be positioned on an external or internal surface of the housing to allow a larger surface area for the antenna. The external device 104 may include a computing device having one or more communication devices that can wirelessly communicate with the glucose monitor 100. In some aspects, the external device 104 may be a handheld computing device, such as a smartphone, personal digital assistant, or tablet. In other aspects, the external device 104 may represent any computing device including, but not limited to, a desktop computer, a laptop, or a wearable device (e.g., a smartwatch). The external device 104 may also include a processor for analyzing measurements received from the glucose monitor 100 or a database for storing such measurement. In FIG. 1, the external device 104 is shown in close proximity to the glucose monitor 100. Arrows 106 represent a wireless coupling of the glucose monitor 100 and the external device 104 for wireless communication between the devices. In some aspects, the coupling range for the coupling of the glucose monitor 100 and the external device 104 may be include a range between 0 and 25 centimeters.

Figure 2:
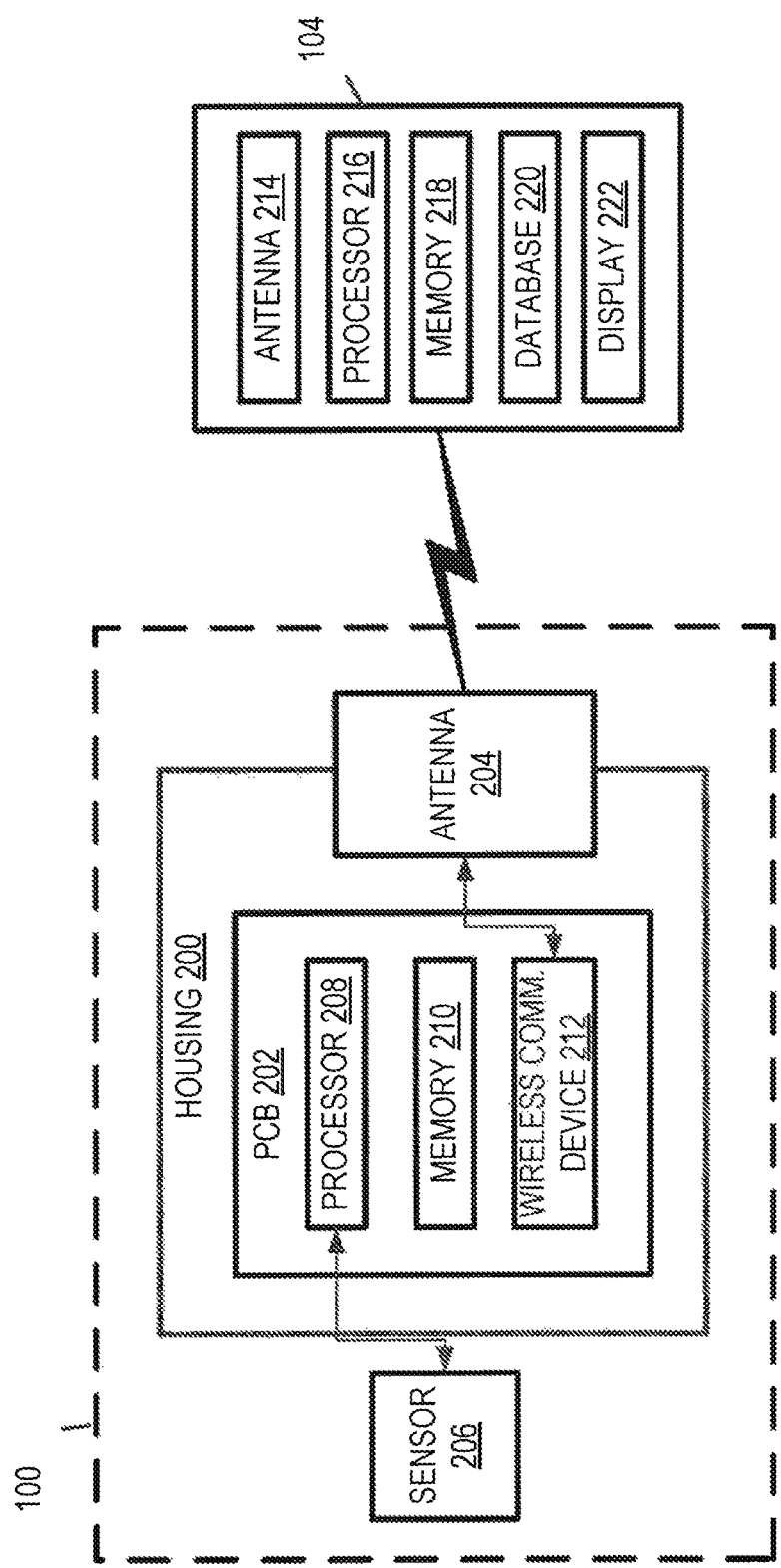
FIG. 2 is a block diagram of the medical device of FIG. 1.

FIG. 2 is a block diagram of the glucose monitor 100 according to aspects of the present disclosure. The glucose monitor 100 includes a housing 200. If desired, the polymer composition of the present invention may form a portion of or the entire housing 200. The housing 200 generally encloses the components of the glucose monitor 100. For example, the housing 200 may include a printed circuit board ("PCB") positioned internal to the housing 200, an antenna 204 positioned on a surface of the housing, and a sensor 206 extending from the housing 200. The housing 200 may have any suitable shape. In some aspects, the housing 200 may include at least one side or section having a linear or planar surface for positioning the housing 200 on the skin 102 of a patient as described in FIG. 1.

The PCB 202 positioned inside the housing 200 may include conductive traces, or other features etched into a surface of the PCB 202 to incorporate the electrical components of the glucose monitor 100. If desired, the polymer composition of the present invention may form a portion (e.g., insulative substrate) of the PCB 202. In one embodiment, the antenna 204 may be positioned on a surface of the housing 200 that operates at a frequency range such as described above. Again, if desired, the polymer composition of the present invention may form a portion (e.g., insulative substrate) of the antenna 204. The sensor 206 may include one or more invasive or non-invasive glucose sensors for measuring a patient's glucose levels. In some aspects, the sensor 206 may include a non-invasive glucose sensor positioned on or proximate to a surface of the skin 102 of the patient to record glucose level measurements. For example, the non-invasive glucose sensor may include a laser or other means for measuring glucose levels without piercing the skin 102. In other aspects, the sensor 206 may include an invasive glucose sensor that may be inserted into the subcutaneous tissue of the skin to extract or interact with electrolytes from the patient to measure glucose levels. For example, the glucose sensor may include one or more electrodes insertable into a patient's skin to expose the electrodes to interstitial fluid. The electrodes may include a glucose oxidase coating to react with glucose present in the interstitial fluid and creates reaction products, such as hydrogen peroxide. A voltage may be applied to the electrodes and an electrical current may be generated based on the amount of the reaction products. The strength of the current may be used to determine the patient's glucose levels. If desired, the polymer composition of the present invention may form a portion (e.g., insulative substrate) of the sensor 206.

The sensor 206 may be coupled to the PCB 202 through a processor 208 positioned on the PCB. In some aspects, the sensor 206 may be coupled to the processor 208 through a conductive wire or other material, such as a spring, extending from the sensor 206 to the processor 208. The processor 208 may receive glucose level measurements from the sensor 206. A wireless communication device 212, such as a transmitter, receiver, or transceiver, may also be mounted to the PCB 202. The wireless communication device 212 may be coupled to the antenna 204 to generate and receive radio signals corresponding to the information (e.g., glucose level measurements) received by the wireless communication device 212. If desired, the polymer composition of the present invention may form a portion (e.g., insulative substrate) of the wireless communication device 212.

The antenna 204 of the glucose monitor 100 may be communicatively coupled to an antenna 214 of the external device 104. The antenna 214 may be of a type compatible to the antenna 204 to allow for communication between the glucose monitor 100 and the external device 104. The external device 104 may also include a processor 216 and a memory 218 including instructions executable by the processor 216. If desired, the polymer composition of the present invention may form a portion (e.g., insulative substrate) of the external device 104. In some aspects, the memory 218 may include instructions for causing the processor 216 to store glucose level measurements of a patient received from the glucose monitor 100 in a database 220. The database 220 may include a storage device having space for storing multiple glucose level measurements. The database 220 may be configured to store glucose level measurements for a single patient or multiple patients. The memory 218 may include instructions for causing the processor 216 to analyze glucose level measurements of a patient received from the glucose monitor 100. For example, the processor 216 may generate one or more user interfaces including graphs, trends, reports, or other analysis of the glucose level measurements received from the glucose monitor 100. The external device 104 also includes a display unit 222 on which the user interfaces generated by the processor 216 may be displayed. In some aspects, the display unit 22 may include a cathode ray tube, a liquid crystal display, light-emitting diodes, organic light-emitting diodes, or other displaying device for displaying the user interfaces.

The following test methods may be employed to determine certain of the properties referenced herein.
Test Methods Melt Viscosity: The melt viscosity (Pa·s) may be determined in accordance with ISO Test No. 11443:2014 at a shear rate of 1,000 s$^{-1}$ and temperature 15° C. above the melting temperature using a Dynisco LCR7001 capillary rheometer. The rheometer orifice (die) had a diameter of 1 mm, length of 20 mm, L/D ratio of 20.1, and an entrance angle of 180°. The diameter of the barrel was 9.55 mm+0.005 mm and the length of the rod was 233.4 mm.

Melting Temperature: The melting temperature ("Tm") may be determined by differential scanning calorimetry ("DSC") as is known in the art. The melting temperature is the differential scanning calorimetry (DSC) peak melt temperature as determined by ISO Test No. 11357-2:2020. Under the DSC procedure, samples were heated and cooled at 20° C. per minute as stated in ISO Standard 10350 using DSC measurements conducted on a TA Q2000 Instrument.

Deflection Temperature Under Load ("DTUL"): The deflection under load temperature may be determined in accordance with ISO Test No. 75-2:2013 (technically equivalent to ASTM D648-18). More particularly, a test strip sample having a length of 80 mm, thickness of 10 mm, and width of 4 mm may be subjected to an edgewise three-point bending test in which the specified load (maximum outer fibers stress) was 1.8 Megapascals. The specimen may be lowered into a silicone oil bath where the temperature is raised at 2° C. per minute until it deflects 0.25 mm (0.32 mm for ISO Test No. 75-2:2013).

Tensile Modulus, Tensile Stress, and Tensile Elongation: Tensile properties may be tested according to ISO Test No. 527:2019 (technically equivalent to ASTM D638-14). Modulus and strength measurements may be made on the same test strip sample having a length of 80 mm, thickness of 10 mm, and width of 4 mm. The testing temperature may be 23° C., and the testing speeds may be 1 or 5 mm/min.

Flexural Modulus, Flexural Stress, and Flexural Elongation: Flexural properties may be tested according to ISO Test No. 178:2019 (technically equivalent to ASTM D790-10). This test may be performed on a 64 mm support span. Tests may be run on the center portions of uncut ISO 3167 multi-purpose bars. The testing temperature may be 23° C. and the testing speed may be 2 mm/min.

Charpy Impact Strength: Charpy properties may be tested according to ISO Test No. ISO 179-1:2010) (technically equivalent to ASTM D256-10, Method B). This test may be run using a Type 1 specimen size (length of 80 mm, width of 10 mm, and thickness of 4 mm). When testing the notched impact strength, the notch may be a Type A notch (0.25 mm base radius). Specimens may be cut from the center of a multi-purpose bar using a single tooth milling machine. The testing temperature may be 23° C.

Rockwell Hardness: Rockwell hardness is a measure of the indentation resistance of a material and may be determined in accordance with ASTM D785-08 (Scale M). Testing is performed by first forcing a steel ball indentor into the surface of a material using a specified minor load. The load is then increased to a specified major load and decreased back to the original minor load. The Rockwell hardness is a measure of the net increase in depth of the indentor, and is calculated by subtracting the penetration divided by the scale division from 130.

Dielectric Constant ("Dk") and Dissipation Factor ("Df"): The dielectric constant (or relative static permittivity) and dissipation factor (or loss tangent) are determined at a frequency of 2 GHz in accordance with IPC 650 Test Method No. 2.5.5.13 (January 2007). According to this method, the in-plane dielectric constant and dissipation factor may be determined using a split-cylinder resonator. The tested sample had a thickness of 8.175 mm, width of 70 mm, and length of 70 mm.

Surface/Volume Resistivity: The surface and volume resistivity values may be determined in accordance with IEC 62631-3-1:2016 or ASTM D257-14. According to this procedure, a standard specimen (e.g., 1 meter cube) is placed between two electrodes. A voltage is applied for sixty (60) seconds and the resistance is measured. The surface resistivity is the quotient of the potential gradient (in V/m) and the current per unit of electrode length (in Nm), and generally represents the resistance to leakage current along the surface of an insulating material. Because the four (4) ends of the electrodes define a square, the lengths in the quotient cancel and surface resistivities are reported in ohms, although it is also common to see the more descriptive unit of ohms per square. Volume resistivity is also determined as the ratio of the potential gradient parallel to the current in a material to the current density. In SI units, volume resistivity is numerically equal to the direct-current resistance between opposite faces of a one-meter cube of the material (ohm-m or ohm-cm).

Heat Cycle Test: Specimens may be placed in a temperature control chamber and heated/cooled within a temperature range of from −30° C. and 100° C. Initially, the samples may be heated until reaching a temperature of 100° C., when they may be immediately cooled. When the temperature reaches −30° C., the specimens may be immediately heated again until reaching 100° C. Twenty three (23) heating/cooling cycles may be performed over a 3-hour time period.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A medical device that is capable of transmitting a radiofrequency signal to and/or receiving a radiofrequency signal from an external device, wherein the medical device comprises at least one component that contains a polymer composition that exhibits a dielectric constant of about 4 or less at a frequency of 2 GHz, wherein the polymer composition includes a liquid crystalline polymer.

2. The medical device of claim 1, wherein the polymer composition exhibits a melt viscosity of 200 Pa-s or less as determined at a shear rate of 400 seconds$^{-1}$ and at a temperature 15° C. higher than the melting temperature of the composition in accordance with ISO Test No. 11443: 2014.

3. The medical device of claim 1, wherein the polymer composition exhibits a tensile modulus of about 8,000 MPa or more as determined in accordance with ISO Test No. 527:2019.

4. The medical device of claim 1, wherein the polymer composition exhibits a tensile strength of from about 150 MPa or more as determined in accordance with ISO Test No. 527:2019.

5. The medical device of claim 1, wherein the polymer composition exhibits a flexural modulus of about 10,000 MPa or more as determined in accordance with ISO Test No. 178:2019 at 23° C.

6. The medical device of claim 1, wherein the polymer composition exhibits a Rockwell surface hardness of about 65 or less as determined in accordance with ASTM D785-08 (Scale M).

7. The medical device of claim 1, wherein the polymer composition exhibits a Charpy unnotched impact strength of about 45 KJ/m$^2$ or more as determined at 23° C. according to ISO Test No. 179-1:2010.

8. The medical device of claim 1, wherein the liquid crystalline polymer has a melting temperature of about 280° C. or more.

9. The medical device of claim 1, wherein the polymer composition exhibits a dissipation factor of about 0.01 or less at a frequency of 2 GHz.

10. The medical device of claim 1, wherein the polymer composition exhibits an electromagnetic interference shielding effectiveness of about 20 decibels or more at a frequency of 2 GHz.

11. The medical device of claim 10, wherein the liquid crystalline polymer contains one or more repeating units derived from a hydroxycarboxylic acid.

12. The medical device of claim 11, wherein the hydroxycarboxylic acid repeating units constitute about 50 mol. % or more of the polymer.

13. The medical device of claim 12, wherein the liquid crystalline polymer contains repeating units derived from 4-hydroxybenzoic acid, 6-hydroxy-2-napthoic acid, or a combination thereof.

14. The medical device of claim 13, wherein the liquid crystalline polymer further contains repeating units derived from terephthalic acid, isophthalic acid, 2,6-naphthalenedicarboxylic acid, hydroquinone, 4,4'-biphenol, acetaminophen, 4-aminophenol, or a combination thereof.

15. The medical device of claim 1, wherein the total amount of repeating units derived from naphthenic hydroxycarboxylic and/or dicarboxylic acids in the liquid crystalline polymer is about 10 mol. % or more.

16. The medical device of claim 1, wherein the polymer composition includes a hollow filler.

17. The medical device of claim 1, wherein the polymer composition includes a mineral filler.

18. The medical device of claim 17, wherein the mineral filler includes particles.

19. The medical device of claim 18, wherein the particles include talc, mica, barium sulfate, or a combination thereof.

20. The medical device of claim 17, wherein the mineral filler includes fibers.

21. The medical device of claim 20, wherein the fibers include wollastonite.

22. The medical device of claim 1, wherein the polymer composition includes glass fibers.

23. The medical device of claim 1, wherein the polymer composition includes an impact modifier.

24. The medical device of claim 1, wherein the polymer composition includes an electrically conductive filler.

25. The medical device of claim 1, wherein the polymer composition includes a laser activatable additive.

26. The medical device of claim 1, wherein the medical device includes a circuit substrate that includes a substrate on which is disposed one or more antenna elements.

27. The medical device of claim 26, wherein the substrate includes the polymer composition.

28. The medical device of claim 1, wherein the medical device includes a housing that encloses at least one component of the device.

29. The medical device of claim 28, wherein the housing contains the polymer composition.

30. The medical device of claim 28, wherein the component includes an electrical element.

31. The medical device of claim 30, wherein the electrical element includes a printed circuit board, sensing circuitry, or a combination thereof.

32. The medical device of claim 30, wherein the electrical element includes the polymer composition.

33. The medical device of claim 1, wherein the medical device includes a sensor that is configured to obtain physiological information from a user.

34. The medical device of claim 33, wherein the physiological information includes heart rate, oxygen saturation, a chemical in blood or subcutaneous interstitial fluid, body temperature, tissue hydration, or a combination thereof.

35. The medical device of claim 1, wherein the medical device includes a drug delivery device.

36. The medical device of claim 35, wherein the medical device includes an injection pen, autoinjector, infusion pump, subcutaneous injection pump, meter dose inhaler, dry powder inhaler, nasal inhaler, iontophoresis patch, or a combination thereof.

37. The medical device of claim 1, wherein the medical device includes a telemetric device.

38. The medical device of claim 37, wherein the medical device includes a home health or hospital monitor, CPAP machine, oxygen concentrator, medicine distribution container, blood pressure cuff, or a combination thereof.

39. A wireless communication medical system comprising the medical device of claim 1 and an external device.

40. The wireless communication medical system of claim 39, further comprising an antenna system that is configured to transmit a radiofrequency signal from the medical device to the external device and/or receive a radiofrequency signal from the external device to the medical device.

41. The wireless communication medical system of claim 39, wherein the medical device contains an antenna system that is configured to transmit a radiofrequency signal from the medical device to the external device and/or receive a radiofrequency signal from the external device to the medical device.

42. The wireless communication medical system of claim 39, wherein the external device includes a desktop computer, portable electronic device, wearable device, or a combination thereof.

* * * * *